US012667701B2

(12) United States Patent
Dezfulian et al.

(10) Patent No.: US 12,667,701 B2
(45) Date of Patent: *Jun. 30, 2026

(54) CATHETER INSERTION SYSTEMS

(71) Applicant: University of Pittsburgh - Of the Commonwealth System of Higher Education, Pittsburgh, PA (US)

(72) Inventors: Cameron Dezfulian, Pittsburgh, PA (US); William W. Clark, Wexford, PA (US); Ehsan Qaium, Pittsburgh, PA (US); Dennis Wist, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 237 days.

This patent is subject to a terminal disclaimer.

(21) Appl. No.: 18/205,285

(22) Filed: Jun. 2, 2023

(65) Prior Publication Data

US 2023/0347111 A1      Nov. 2, 2023

Related U.S. Application Data

(63) Continuation of application No. 16/623,611, filed as application No. PCT/US2018/040952 on Jul. 5, 2018, now Pat. No. 11,701,494.

(Continued)

(51) Int. Cl.
A61M 25/06          (2006.01)
A61M 25/09          (2006.01)

(52) U.S. Cl.
CPC .. A61M 25/0606 (2013.01); A61M 25/09041 (2013.01); A61M 2205/273 (2013.01);

(Continued)

(58) Field of Classification Search
CPC ........ A61M 25/0606; A61M 25/09041; A61M 2205/273; A61M 2205/3538;

(Continued)

(56) References Cited

U.S. PATENT DOCUMENTS 3,924,606 A    12/1975    Silva et al.
5,063,937 A    11/1991    Ezenwa et al.
(Continued)

FOREIGN PATENT DOCUMENTS

EP          0646382 A1     4/1995
WO      WO 00/47254       8/2000
(Continued)

OTHER PUBLICATIONS

Extended Search Report for EP Application No. 19799231.6, 8 pages, mailed Jan. 27, 2022.

(Continued)

*Primary Examiner* — Theodore J Stigell
(74) *Attorney, Agent, or Firm* — Klarquist Sparkman, LLP

(57)          ABSTRACT

Disclosed catheter insertion systems enable the user to identify the location of the needle based on the electrical properties of subcutaneous tissue relative the electrical properties of other fluids such as blood or air. Disclosed systems can include one or more of the following features: 1) the catheter assembly is modular (e.g., the catheter can be connected and disconnected from the detection unit at will); 2) the detection unit employs an electrical circuit that allows for the discernment between subcutaneous tissue and blood; 3) the system assists the end user with catheter advancement. Some embodiments can be used to insert catheters into a spaces where the needle passes first through subcutaneous fat and muscle before entering fluid or air.

20 Claims, 27 Drawing Sheets

10

200

300

100

Related U.S. Application Data

(60) Provisional application No. 62/529,962, filed on Jul. 7, 2017.

(52) U.S. Cl.
CPC ............... *A61M 2205/3538* (2013.01); *A61M 2205/3553* (2013.01); *A61M 2205/3653* (2013.01); *A61M 2205/581* (2013.01); *A61M 2205/582* (2013.01); *A61M 2205/583* (2013.01); *A61M 2205/6027* (2013.01)

(58) Field of Classification Search
CPC .. A61M 2205/3553; A61M 2205/3653; A61M 2205/581; A61M 2205/582; A61M 2205/583; A61M 2205/6027; A61B 5/0537; A61B 5/065; A61B 5/6876; A61B 5/6851; A61B 5/6848; A61B 5/6852; A61B 5/7225; H03F 3/45475
See application file for complete search history.

(56) References Cited

U.S. PATENT DOCUMENTS

| | | | |
|---|---|---|---|
| 5,271,413 | A | 12/1993 | Dalamagas et al. |
| 5,335,668 | A | 8/1994 | Nardella |
| 5,589,639 | A | 12/1996 | D'Antonio et al. |
| 5,935,066 | A | 8/1999 | Harris |
| 6,024,704 | A | 2/2000 | Meador et al. |
| 6,337,994 | B1 | 1/2002 | Stoianovici et al. |
| 6,373,264 | B1 | 4/2002 | Matsumoto et al. |
| 6,847,841 | B1 | 1/2005 | El Hatw |
| 7,845,537 | B2 | 12/2010 | Shelton, IV et al. |
| 8,323,279 | B2 | 12/2012 | Dahla et al. |
| 8,489,172 | B2 | 7/2013 | Gelbart et al. |
| 9,597,482 | B2 | 3/2017 | Hann |
| 10,022,059 | B2 | 7/2018 | Fischell et al. |
| 10,154,792 | B2 | 12/2018 | Sakai et al. |
| 10,271,866 | B2 | 4/2019 | Clark, III et al. |
| 10,434,278 | B2 | 10/2019 | Dunbar et al. |
| 11,517,722 | B2 | 12/2022 | Ma et al. |
| 11,547,787 | B2 | 1/2023 | Turer et al. |
| 11,701,494 | B2 * | 7/2023 | Dezfulian ............ A61B 5/6852 604/164.13 |
| 2001/0049510 | A1 | 12/2001 | Burr et al. |
| 2002/0046756 | A1 | 4/2002 | Laizzo et al. |
| 2005/0267455 | A1 | 12/2005 | Eggers et al. |
| 2007/0225686 | A1 | 9/2007 | Shippert et al. |
| 2008/0306391 | A1 | 12/2008 | Hular et al. |
| 2009/0036794 | A1 | 2/2009 | Stubhaug et al. |
| 2009/0118610 | A1 | 5/2009 | Karmarkar et al. |
| 2009/0192441 | A1 | 7/2009 | Gelbert et al. |
| 2010/0286507 | A1 | 11/2010 | Paassilta et al. |
| 2012/0108950 | A1 | 5/2012 | He et al. |
| 2013/0226114 | A1 | 8/2013 | Massi et al. |
| 2013/0310749 | A1 | 11/2013 | Vecchio |
| 2014/0081244 | A1 | 3/2014 | Voeller et al. |
| 2014/0371726 | A1 | 12/2014 | Lee, II |
| 2015/0025521 | A1 | 1/2015 | Friedrichs et al. |
| 2015/0173636 | A1 | 6/2015 | Mokelke et al. |
| 2015/0216442 | A1 | 8/2015 | Lavy et al. |
| 2015/0314105 | A1 | 11/2015 | Gasparyan et al. |
| 2015/0359991 | A1 | 12/2015 | Dunbar et al. |
| 2015/0362448 | A1 | 12/2015 | Lee et al. |
| 2016/0029920 | A1 | 2/2016 | Kronstrom et al. |
| 2016/0096010 | A1 | 4/2016 | Klein |
| 2016/0135842 | A1 | 5/2016 | Kassab |
| 2016/0158502 | A1 | 6/2016 | Kume et al. |
| 2017/0333623 | A1 | 11/2017 | Kamen et al. |
| 2017/0354379 | A1 | 12/2017 | Goyal et al. |
| 2018/0125575 | A1 | 5/2018 | Schwartz et al. |
| 2018/0317801 | A1 | 11/2018 | Lee et al. |
| 2019/0046759 | A1 | 2/2019 | Royer |
| 2019/0247088 | A1 | 8/2019 | Monteiro |
| 2020/0206471 | A1 | 7/2020 | Dezfulian et al. |
| 2021/0330977 | A1 | 10/2021 | Sinha |
| 2023/0149620 | A1 | 5/2023 | Turer et al. |
| 2023/0347111 | A1 | 11/2023 | Dezfulian et al. |

FOREIGN PATENT DOCUMENTS

| | | |
|---|---|---|
| WO | WO 2009/019707 | 2/2009 |
| WO | WO 2012/092948 | 7/2012 |
| WO | 2016034910 | 3/2016 |
| WO | 2016040394 | 3/2016 |
| WO | WO 2019/010330 | 1/2019 |
| WO | WO 2019/217883 | 11/2019 |
| WO | WO 2022/221452 | 10/2022 |

OTHER PUBLICATIONS

Injeq IQ-Needle™ Precision. Care. Confidence., https://injeq.com/, 5 pages, downloaded Mar. 18, 2019.

International Search Report and Written Opinion for related International Application No. PCT/US2018/040952, 9 pages, mailed Oct. 28, 2018.

International Search Report and Written Opinion for International Application No. PCT/US2019/031815, 8 pages, mailed Sep. 22, 2019.

Sharp et al., "Tissue type determination by impedance measurement: A bipolar and monopolar comparison," Saudi Journal of Anesthesia 11: 15-20, 2017.

Trebbels et al., "Real-Time Cannula Navigation in Biological Tissue with high temporal and spatial resolution based on Impedance Spectroscopy," 32nd Annual International Conference of the IEEE EMBS, Buenos Aires, Argentina, 4 pages (Aug. 31-Sep. 4, 2010).

* cited by examiner

204

202

203

203

204

205

208

203
204

CATHETER INSERTION SYSTEMS

CROSS-REFERENCE TO RELATED APPLICATIONS

This application is a continuation of U.S. patent application Ser. No. 16/623,611, filed on Dec. 17, 2019, which is the U.S. National Stage of International Application No. PCT/US2018/040952 filed Jul. 5, 2018, which claims the benefit of U.S. Provisional Patent Application No. 62/529,962 filed Jul. 7, 2017. Each of the above-listed applications is incorporated by reference herein in its entirety.

ACKNOWLEDGMENT OF GOVERNMENT SUPPORT

This invention was made with government support under Grant No. IIP1449702 awarded by the National Science Foundation. The government has certain rights in the invention.

FIELD

This disclosure is related to the field of catheter insertion systems.

BACKGROUND

Many physicians use peripheral intravenous catheters (pIV) to administer lifesaving drugs in a rapid manner. Although millions of pIV's are placed on a daily basis around the world, approximately 25% of patients require multiple attempts to obtain a (pIV). Failure to correctly place an IV the first time increases the patient's pain and the cost associated with the procedure.

Peripheral vascular access is the mainstay of rapid drug delivery in modern healthcare and absolutely essential for inpatient/emergency room care and in certain outpatient settings. Yet placement of a peripheral intravenous catheter (pIV) to facilitate this is challenging despite a nearly universal mandate that all inpatients have a pIV in anticipation of medical emergencies. Approximately 25% of patients require multiple attempts to obtain a pIV resulting in a reported average of 2.2 attempts per successful pIV placement. When one considers the 1.2 billion pIV's purchased worldwide last year, this amounts to a staggering number of failures and a sizable problem within healthcare.

The cost of this difficulty is substantial. Failure to obtain peripheral vascular access subjects patients to increasing pain and distress such that most patients rate pIV placement as their most painful hospital procedure. Delayed pIV placement delays therapy (e.g. antibiotics, blood, resuscitation fluids and medications), which in a number of studies is linked to worsened clinical outcomes. The financial costs of failed pIV attempts are also substantial and largely stem from the personnel time involved with repeated attempts rather than the trivial (~$2) cost of a catheter. In children, the median cost of pIV placement was $41 with 72% of the patients having success with 1 or 2 attempts. But this 72% accounted only for 53% of the costs. The other half came from the 28% of patients requiring ≥3 pIV attempts costing $69-125 for each patient. These personnel costs are not reimbursed. Insurers pay hospitals for a diagnostic code (e.g. pneumonia) that is structured to account for all costs associated with treating the diagnosed condition. If a nurse spends 30 minutes to place a pIV to give antibiotics the hospital reimbursement is no different than if that pIV had been placed within a minute. Failure to place pIV's results in escalation to midline or central venous access which carries greater risk to the patient, time for the practitioner, and cost to the hospital. More challenging IV placement also results in shorter dwell time (IV durability). Finally, difficulty in placing pIV results in higher rates of complications such as phlebitis, thrombosis, infection, and drug extravasation which in the most severe circumstances results in limb amputation. Furthermore, infiltration (medication leaking to surrounding tissue due to improper placement or dislodged catheter) is believed to be a common event that is massively under reported.

In most hospitals, pIV placement is performed primarily by nurses. Larger hospital systems often employ teams of IV nurses. These nurses are very good at prospectively identifying difficult pIV cases, and risk factors for "difficult" pIV access are well known and include pediatric, elderly, obesity, sickle cell anemia, IV drug abuse, prior hospitalizations and diabetic patients. This is important in that nurses can therefore define which patients warrant use of a novel technology like the present invention to maximize benefits while minimizing costs.

As an example, a typical IV nurse team may be a 4-person group. If the team can identify the difficult patients and if a device were available that would allow insertions on the first attempt for these patients, then the IV teams could be reduced to 3 people.

Improving first-time pIV access and durability can result in reduction in patient pain and adverse events, improved outcomes, and reduced institutional legal risk and financial costs. Interviews were conducted with 50 hospital staff (including 32 nurses and 7 members of IV teams) to determine the root cause of failed pIV attempts. The number one reason was inability to advance the IV catheter after an initial blood flash in the needle (see the following section for how pIV's are currently placed) which the operators attributed to 1) passing through the vein by the time the flash was visualized, 2) glancing or tearing the vein with manipulations, and 3) being too shallow in the vein. Other issues identified included vein rolling, vein size too small or fragile to support the catheter, and patient movement.

One solution to assist with catheter placement which has been in use since 1953 is the Seldinger technique, which involves the placement of a guidewire through a needle into the blood vessel or space where one wishes to place a catheter followed by catheter insertion over the guidewire. Since insertion of the flexible guidewire is less traumatic to the vessel and the size is smaller than the needle with a length far longer than the bevel, this reduces vessel trauma and improves success in catheterization. The Seldinger technique required an elaborate sterile field. Integrated units which incorporate a guidewire contained in a sterile sheath, which sits within a traditional catheter over needle design, permits sliding in the guidewire followed by catheterization without the need for sterile setup. Such devices are currently in use for arterial and venous access. However, in the case of venous access these systems fail most often due to failure to recognize vein entry based on blood return or premature sliding of the guidewire resulting in infiltration.

There is therefore a need for improved detection and insertion systems, especially ones that can address the inability to recognize vein entry and to assist the user with timely advancement of a guidewire to facilitate catheterization within fragile or small veins thus addressing the primary deficiencies.

SUMMARY

Disclosed are catheter insertion systems that enable the user to identify the entry of a percutaneously inserted needle containing an integrated guidewire into a fluid or air filled space, such as a blood vessel or pneumothorax, based on the electrical properties of the subcutaneous tissue relative the electrical properties of the fluid (e.g. blood) or air which are sensed by a current passed between the needle and guidewire. Various embodiments of needles and detection units are described. Disclosed systems can include one or more of the following features: 1) the catheter assembly is modular (e.g., the catheter can be connected and disconnected from the detection unit at will); 2) the detection unit employs an electrical circuit that allows for the discernment between subcutaneous tissue and various fluids such as blood, pleural or pericardial effusions or air; and 3) the system assists the end user with catheter advancement via the integrate guidewire. Modified versions of this system can also be employed to insert catheters into a variety of additional spaces where the needle passes first through subcutaneous fat and muscle before entering fluid or air. These include placement of thoracostomy catheters into pleural effusions or pneumothoraces, insertion of catheters into the cerebrospinal fluid or epidural space, insertion of arterial catheters, insertion of pericardiocentesis catheters into a pericardial effusion, insertion of a peritoneal catheter into peritoneal fluid and insertion of percutaneous tracheostomy tubes.

The foregoing and other objects, features, and advantages of the disclosed technology will become more apparent from the following detailed description, which proceeds with reference to the accompanying figures.

BRIEF DESCRIPTION OF THE DRAWINGS

FIG. 12A is an enlarged view of the electrodes with the inside of the needle housing coated with an insulating material while the guide wire (acting as the second electrode) is uncoated. FIG. 12B is a side view of the needle and wire catheter unit.

FIG. 14A shows a disposable catheter unit in nominal position before deployment. FIG. 14B shows the guidewire deployed. FIG. 14C shows the needle and guide wire being removed once catheter is advanced into the vein. FIG. 14D shows the catheter placed in the vein once the needle and guidewire are removed.

FIG. 16A is an isometric view, FIG. 16B is an enlarged view of the electrode, and FIG. 16C. is a section view of the two wired needle.

FIG. 17A shows the wires submerged in Plasma-Lyte A, FIG. 17B shows the wires puncturing pork shoulder muscle, and FIG. 17C shows the wires puncturing pork fat.

FIG. 25A shows pork fat sitting on top of a channel of Plasma-Lyte A. FIG. 25B shows a catheter needle connected to the detection unit puncturing the fat prior to entering the Plasma-Lyte A channel.

DETAILED DESCRIPTION

Figure 1:
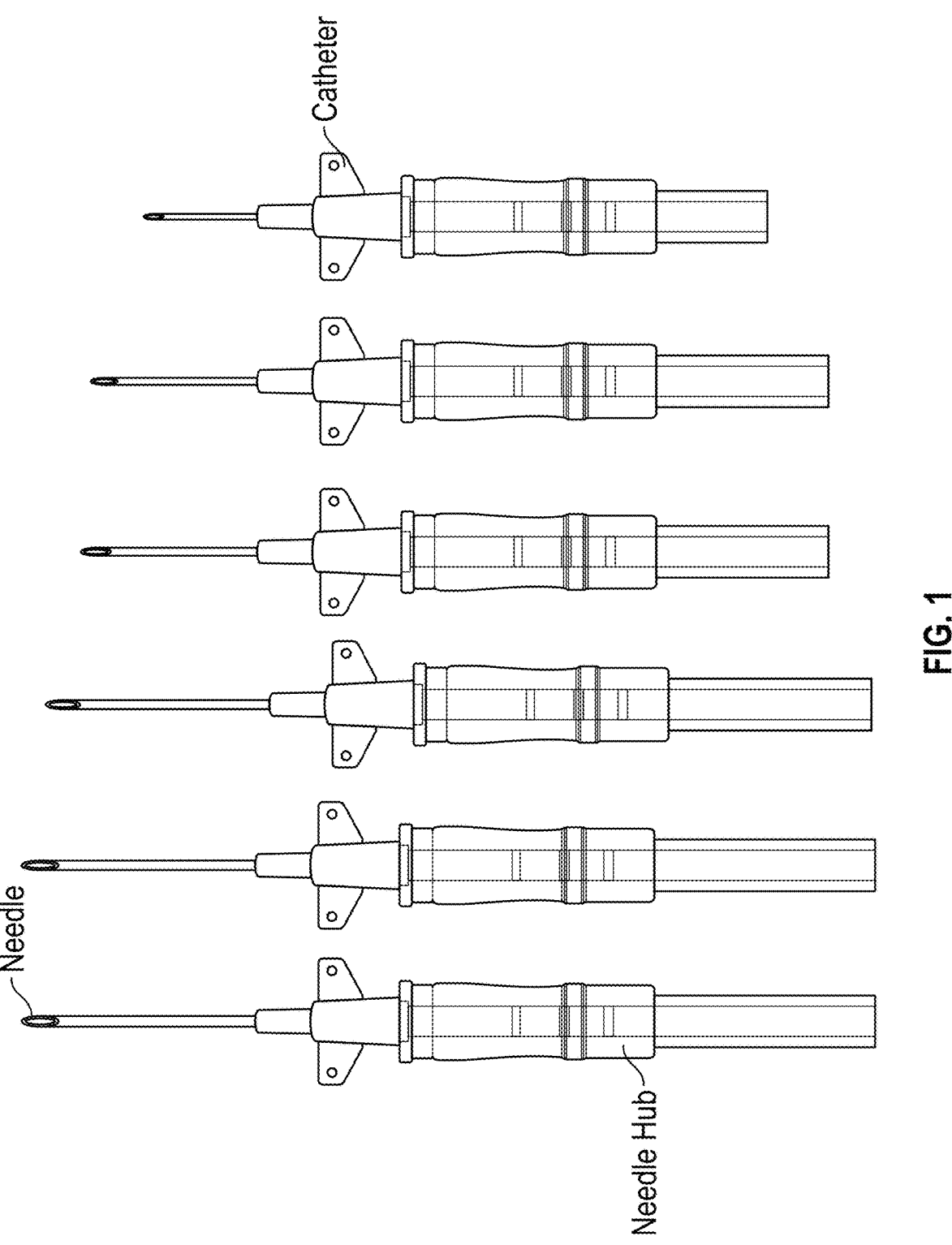
FIG. 1 shows standard pIVs in clinical use. pIVs are arranged from 14 (left) to 24 (right) gauge. The catheter sits over the needle a small distance back from the hub.

A conventional pIV (see FIG. 1) is placed by inserting the needle into a vein. As venous blood flows into the needle and enters the clear chamber (the "hub") this is called the "flash". The user recognizes the flash as evidence of vein entry then advances the catheter into the vein.

The catheter is slightly larger than the needle diameter and set back from the tip of the needle such that the needle may enter the vein without the catheter being in the vessel thus preventing advancement. The "flash" depends on venous pressure, which must be sufficient to drive blood flow into the clear chamber through the needle. Normal venous pressure is only 2-3 mm Hg, but can be lower in patients experiencing shock or dehydration. Visualization of the "flash" can be delayed or prevented by high needle resistance found in smaller gauge IVs such as those employed in pediatrics. As a result, many users continue to advance the needle until passing through the vein before visualizing a flash resulting in a "blown vein."

Once the needle is inserted into the vein the catheter is advanced over the needed and into the vein. Though tapered, the catheter can be larger than the hole in the vein, which can cause some resistance to entry, at times injuring or tearing the vein, which is an additional complication that may occur. When the catheter is sufficiently inserted, the needle can then be removed and tubing is connected to the catheter for administration of medications and fluids.

As discussed, the inability to advance the catheter after an initial blood flash attributed to the catheter not yet being in the anterior portion of the vein, passing through the posterior portion of the vein ("blown vein"), glancing or tearing the vein due to resistance to catheter advancement, and medication leaking into surrounding tissue as a result of a shallow position within the vein resulting in subsequent dislodgement (infiltration) represent the major failures in the present technology that result in failed first attempts.

Technologies intended to improve pIV placement include ultrasound guidance and integrated Seldinger devices (e.g., devices marketed under the name AccuCath). However, present ultrasound technology, when used in cross section often does not permit the user to recognize vessel entry so blood return is still sought after. Ultrasound use in longitudinal section (section obtained by slicing in any plane parallel to the vertical axis) is extremely challenging for small veins even for seasoned clinicians. Furthermore, ultrasound does nothing to assist in catheter advancement. As a result, even with extensive training ultrasound employed in "difficult" patients has been shown to have a first attempt pIV failure rate of 31% and 29% in adults and 58% in pediatrics. In addition, additional time (2-4 min) is required for use of ultrasound as it requires an additional device and added sterile precautions. In a center using ultrasound routinely, nurses still regard 22% of patients to be "difficult" to obtain vascular access.

Figure 2:
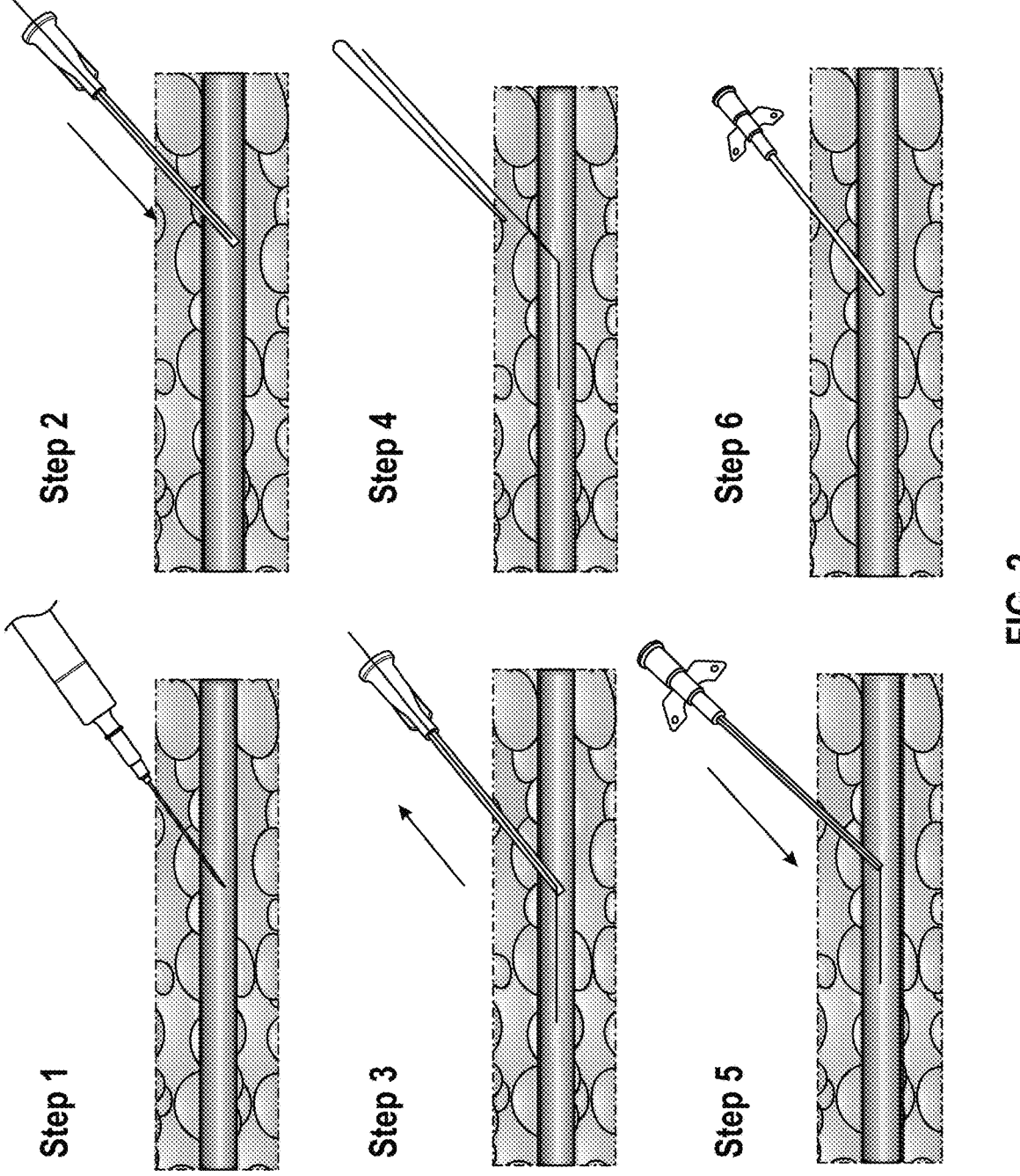
FIG. 2 illustrates a Seldinger technique. Step 1) the needle is inserted into the skin at a 45 degree angle, and negative pressure is applied until blood return is visualized inside the syringe. Step 2) the syringe is removed and guide wire is inserted. Step 3) once guidewire has been advanced to a desired length, the needle is withdrawn. Step 4) Insertion site is enlarged using a scalpel as necessary for large catheters. Step 5) while holding the guidewire, the catheter is advanced into the vein. Step 6) the guidewire is withdrawn and blood return is sought after to verify catheter placement.

Most often during central venous or arterial catheter placement, the Seldinger technique is employed by the end users in order to obtain access to veins. The Seldinger technique (see FIG. 2) involves six individual steps which are described below.

Step 1) the needle is inserted into the skin at a 45 angle, and negative pressure is applied until blood return is visualized inside the syringe.

Step 2) the syringe is removed and guidewire is inserted into the vein through the needle.

Step 3) once guidewire has been advanced to a desired length, the needle is withdrawn while holding the guidewire.

Step 4) Using a scalpel and dilator, the insertion site is enlarged as necessary for large catheters.

Step 5) the catheter is advanced into the artery/vein using the guide wire.

Step 6) the guidewire is withdrawn and blood return is sought after to verify catheter placement.

The Seldinger technique can require a complete sterile set up and considerable training. A simple integrated Seldinger system exists that integrates the guidewire into the plastic chamber behind the needle (where blood return is visualized). Such "AccuCath" systems suffer from the shortcoming that the integrated guidewire creates and additional obstruction to blood flow. In the setting of low venous blood pressure (2-3 mm Hg) this prevents the user from visualizing the blood flash. The disclosed technology obviates the need to visualize the flash confirming vein entry by change in electrical resistance and notifying the user through a light, sound or vibration (selected by the user). Thus the guide wire in the Seldinger technique can be adopted to gain its advantages in catheter placement while overcoming the disadvantage created by obstructing blood return.

In the field, paramedics have turned to intraosseous (i.e. needle into bone; IO) access due to randomized trials demonstrating 91% first attempt success with IO placement after cardiac arrest vs. 43% first-attempt success rate for pIV. As a result, in emergency situations the present recommendations have shifted to favor IO placement rather than standard pIV. But IO access is not a primary alternative to pIV's due to the increased discomfort experienced by the patient.

In some situations, vein finders use near infrared light (e.g., 628 nm) to visualize veins. However, these devices merely identify where a vein is—they do not necessarily help with placement of a device in the vein. As a result, near-infrared vein finder devices have been found to not improve cannulation, thus failing to address the root causes of pIV placement failure.

In some applications, the disclosed technology can be applied to the "difficult" patient when it comes to establishing pIV vascular access. Roughly 25% of all patients fit this category where multiple attempts are required. Fortunately, these patients can be prospectively identified by skilled nurses. If one uses the conservative (because it only reflects adults and excludes more challenging pediatrics) 2.2 pIV attempts per patient, then the 1.2 billion pIV systems purchased worldwide annually reflect 545 million patients, 136 million of whom fall into the "difficult" category (i.e. expected to require multiple attempts).

The disclosed technology can improve patient care and outcomes as well as healthcare system performance by accelerating successful pIV placement, which can result in one or more of the following benefits/advantages:

1. Reduced patient pain perception, bruising and hence improved satisfaction.

2. Reduced adverse events including infiltrations, phlebitis, infections and bruising all of which are associated with multiple pIV attempts. Though uncommon, extravasation of caustic agents can result in significant litigation.

3. More rapid delivery of potentially life-saving therapies such as blood, fluid or antibiotics.

4. Reduction in cost to healthcare systems that are not reimbursed for failed attempts. This cost savings would be realized for example by the ability to reduce staffing on the IV team from 4 to 3 nurses per shift.

Figure 3:
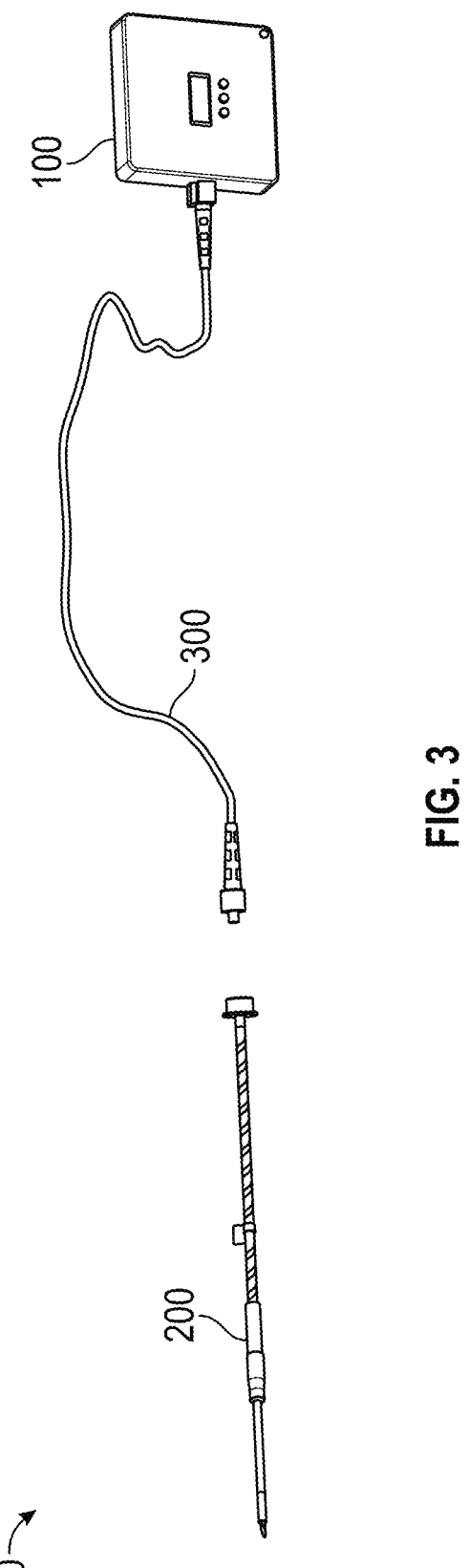
FIG. 3 is a schematic of an exemplary system including a detection unit, disposable catheter unit, and wires providing electrical connection.

FIG. 3 shows an exemplary catheter insertion system (10) that comprises a detection unit (100), a disposable catheter unit (200), and wires providing the electrical connection to the detection unit (300). Several exemplary system combinations are presented in this application for the detection unit and the disposable catheter unit, both of which are described below in greater detail.

The catheter insertion system 10 measures the resistance of materials that the needle contacts as it is inserted. The resistance values can be used to indicate progress of the needle through subcutaneous tissue and into the vein and in contact with blood. This information can be used through various algorithms and hardware to allow the IV nurse to successfully place the catheter on the first attempt.

The tissue or fluid resistance constitutes a resistor that can be measured by different techniques. Some embodiments of the detection circuit (described below) contain an oscillator whose frequency of oscillation depends on the quantities of connected resistor and capacitor components. In some embodiments, the tissue or fluid resistance between the needle and guide wire make up a key resistor component in the circuit. Different resistances (e.g. fatty tissue under the skin vs. blood inside the vessel) cause the frequency of oscillation to change. By measuring this frequency, the type of tissue in contact with the needle, and thus the location of the needle can be determined.

Figure 4:
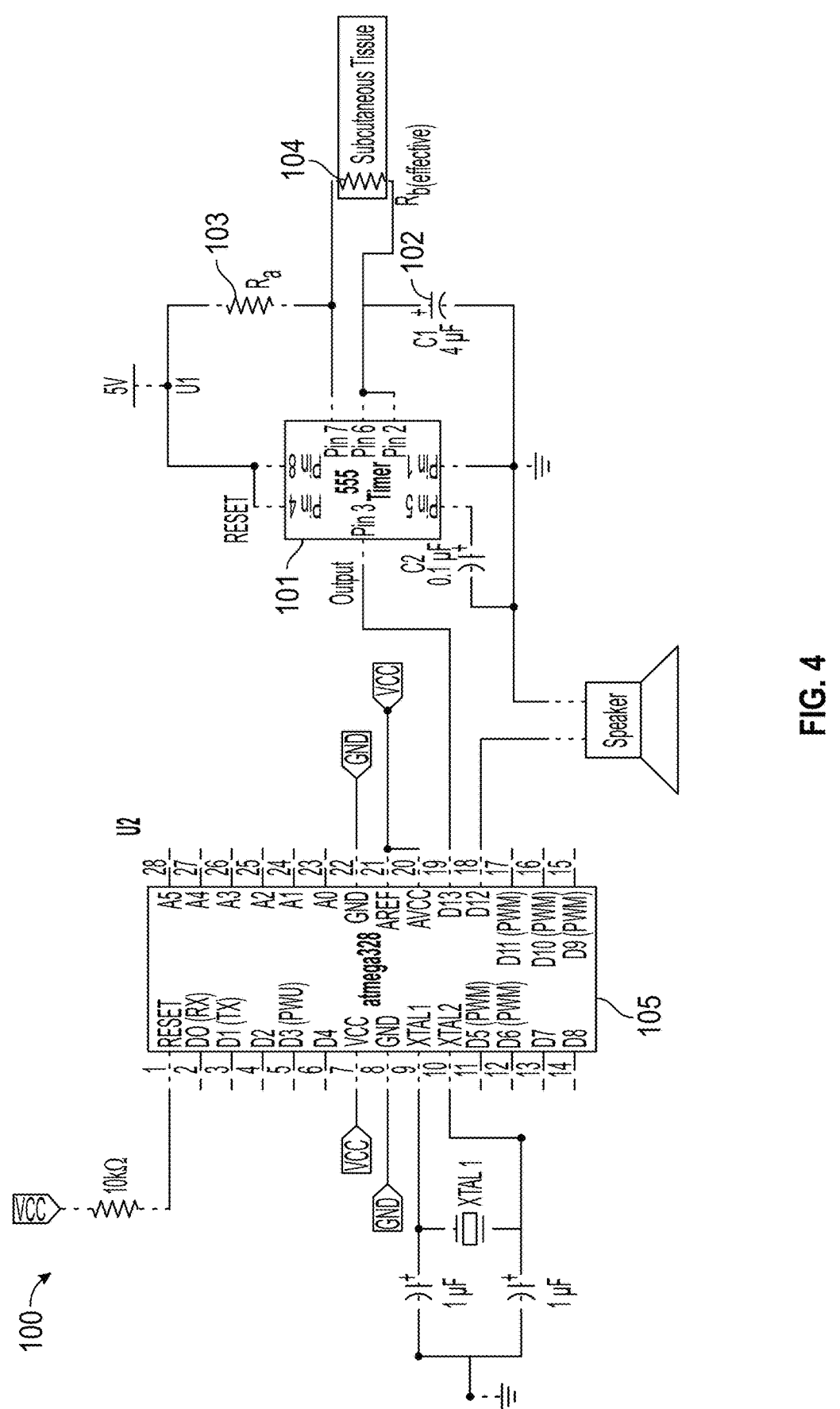
FIG. 4 is a circuit diagram of a 555 timer circuit in astable mode where $R_b$ is made up of the tissue resistance between the needle and guidewire ($R_{effective}$). The signal from the timer circuit can be sent to a micro controller, which can measure the frequency and alert the user to a change through an audible tone.

FIG. 4 displays an example of a circuit diagram (as described above) for the detection unit (100), although other timing circuits may be used. The circuit 100 includes a timer chip (101) (for example a 555 chip), a capacitor of predetermined value (for example a 4.7 μF capacitor) (102), resistors $R_a$ (pre-determined, for example 675Ω) (103), $R_{effective}$ (104) the unknown resistance of the tissue and a microcontroller (105). As shown in FIG. 4, the needle and guidewire are connected to the circuit through extension wires and the tissue/fluid resistance becomes the effective resistance $R_{effective}$. Although only subcutaneous tissue is shown in the figure, it should be noted that the needle encounters other materials such as blood and muscle during use. The 555 is a timer chip that is used to generate time delays or oscillation. It has two modes of operation, mono stable (time delay), and astable (oscillator). A preferred use of this timer chip in conjunction with the disclosed catheter insertion systems is in a stable mode.

Figure 5A:
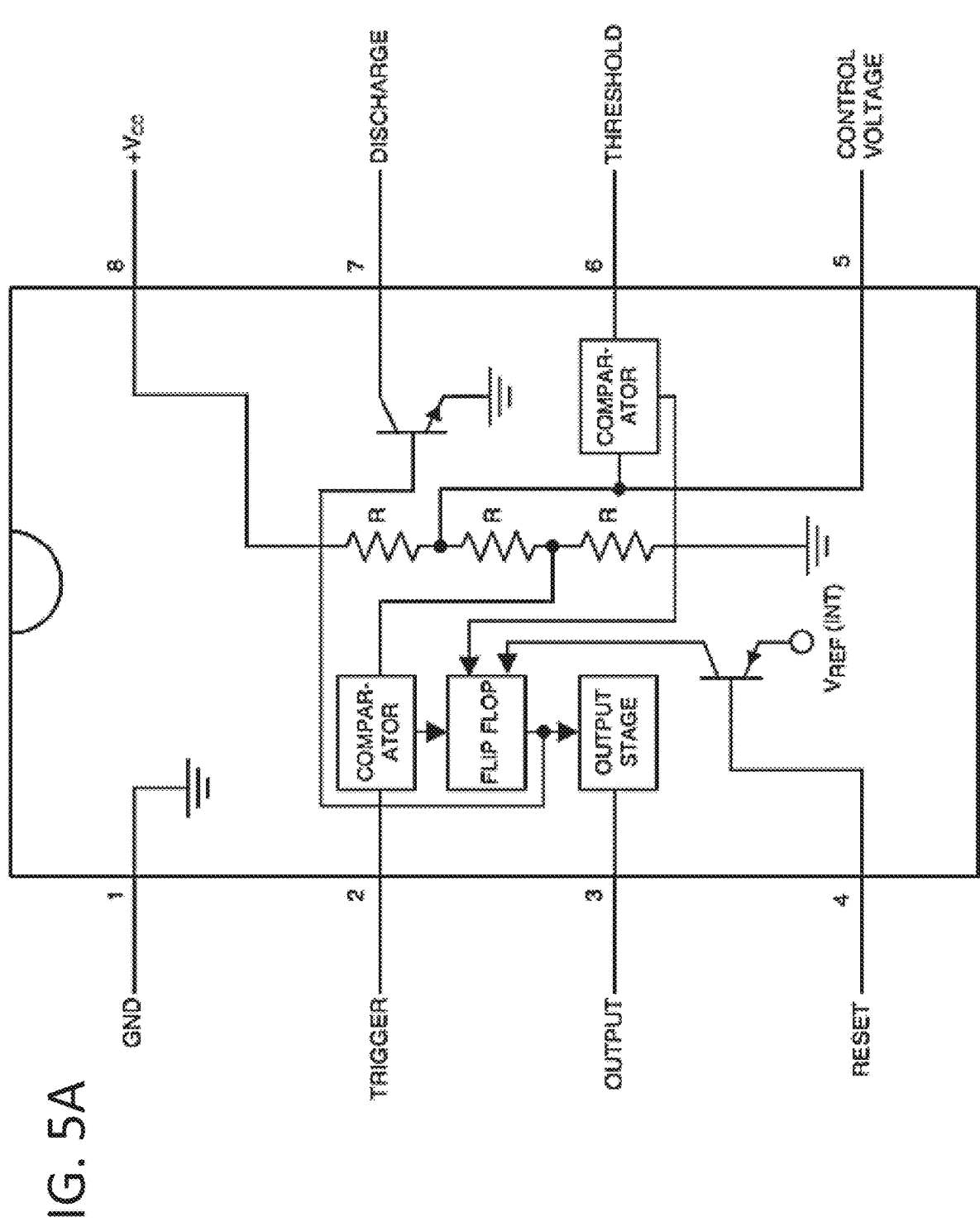
FIG. 5A illustrates an internal circuit diagram of a 555 timer.

The operation of an exemplary 555 timer chip (as well as other example timer circuits) is described here to clarify how it is used to measure tissue/fluid resistance in the catheter insertion systems. FIG. 5A displays the internal circuitry of the 555 timer. The internal circuit of the timer can include three 5KΩ resistors, two comparators that compare two input voltages (labeled V+ and V−), a flip flop, an output stage and two transistors. In a stable mode, a voltage (Vcc) is provided across the resistors $R_a$ (103) and $R_{effective}$ (the unknown tissue/fluid resistance) (104), which in turn starts charging the capacitor (102). Once the capacitor reaches some percentage (for example ⅔) of the supply voltage it discharges through the transistor in pin 7 and $R_{effective}$. Once discharged the capacitor starts re-charging through resistors $R_a$ and $R_{effective}$. While the capacitor is charging, the first comparator connected to pin 2 compares the input voltage from the trigger pin to a reference voltage that may be some percentage (for example ⅓) of Vcc. At the same time, the second comparator compares the input voltage from the threshold pin (pin 6) to a reference voltage (for example ⅔) of Vcc from the voltage divider. When the input voltage (V+) is higher than the reference voltage (V−) the comparator outputs a logic 1 or if V− is higher than V+ then the comparator outputs a logic 0.

The outputs from the two comparators are connected to the flip flop which produces either a logic 1 or a logic 0 signal based on the state of the inputs. Next, the output signal from the flip flop travels to the output stage. When the output stage receives a logic input of 0 from the flip flop it outputs a digital high voltage at that time. Subsequently when a logic input of 1 is received by the output stage, pin 3 is set to a digital low voltage, and the transistor in pin 7 is opened allowing the capacitor to discharge. This process continuously repeats while the timer is operating in astable mode producing a clocking signal (oscillating binary output in the form of a rectangular wave) outputted via pin 3 whose signal is sent to a microcontroller (e.g., ATmega328p). The frequency of the rectangular wave is dependent on the relative values of the resistors (103 and 104) and the capacitor (102) and in this scenario is used specifically to determine the resistance or change in resistance of the unknown tissue (104). Other component values can be determined using related methods.

An alternative approach to the 555 timer is to use an operational amplifier. An operational amplifier (op-amp) is a common integrated circuit which can be combined with external discrete components to create a wide variety of signal processing circuits.

The op-amp is an active electrical component that can have connection to an external power device.

Figure 5B:
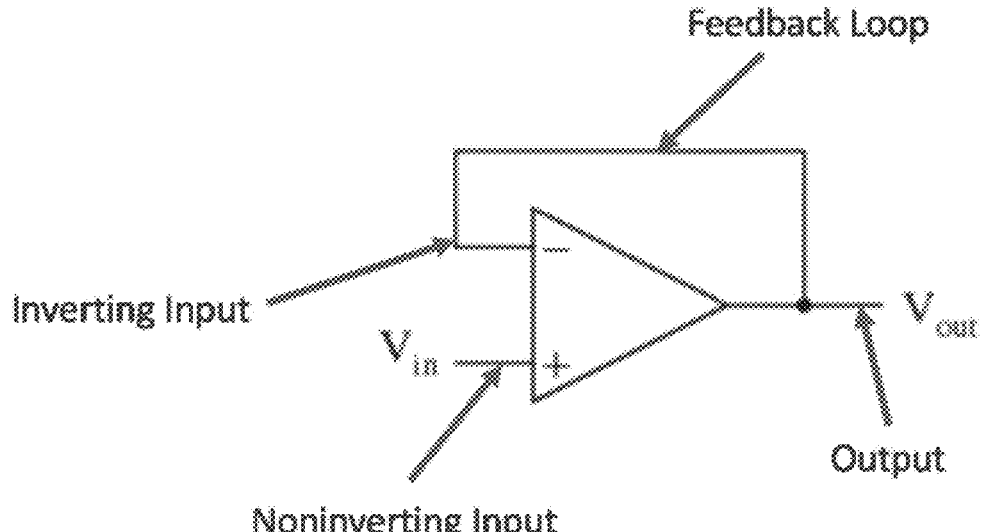
FIG. 5B illustrates an electrical schematic of an Op-amp with a feedback loop.

FIG. 5A displays the basic electrical schematic of an operational Amplifier. FIG. 5B shows an inverting and noninverting input, an output, and a feedback loop to stabilize the output.

For the exemplary applications disclosed herein, the op-amp can be operated as an astable oscillator. The operation of the op-amp is described below to clarify how it is used to measure tissue/fluid resistance in the catheter insertion systems.

Figure 5C:
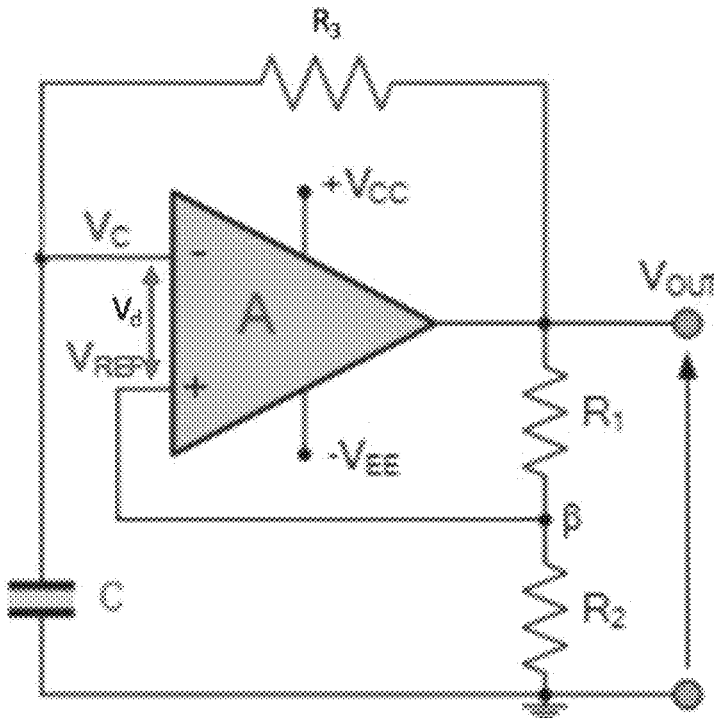
FIG. 5C illustrates an electrical schematic of an Op-amp as an astable oscillator.

FIG. 5C displays the schematic of an op-amp as an oscillator. The op-amp multivibrator is an astable oscillator circuit that generates a rectangular output waveform that switches between supply voltages $+V_{CC}$ to $-V_{EE}$, using an RC timing network.

The period of the waveform is determined by the charge/discharge rate of the capacitor, which depends on the circuit components as shown in Equation 1, and the frequency of the waveform is found by taking the inverse of the time period as shown by Equation 2.

$$T = 2R_3C \ \ln\left(\frac{1+\beta}{1-\beta}\right) \tag{1}$$

$$f = \frac{1}{T} = \frac{1}{2R_3C \ \ln\left(\frac{1+\beta}{1-\beta}\right)} \tag{2}$$

where β is defined as $$\beta = \frac{R_2}{R_1 + R_2} \tag{3}$$

Figure 5D:
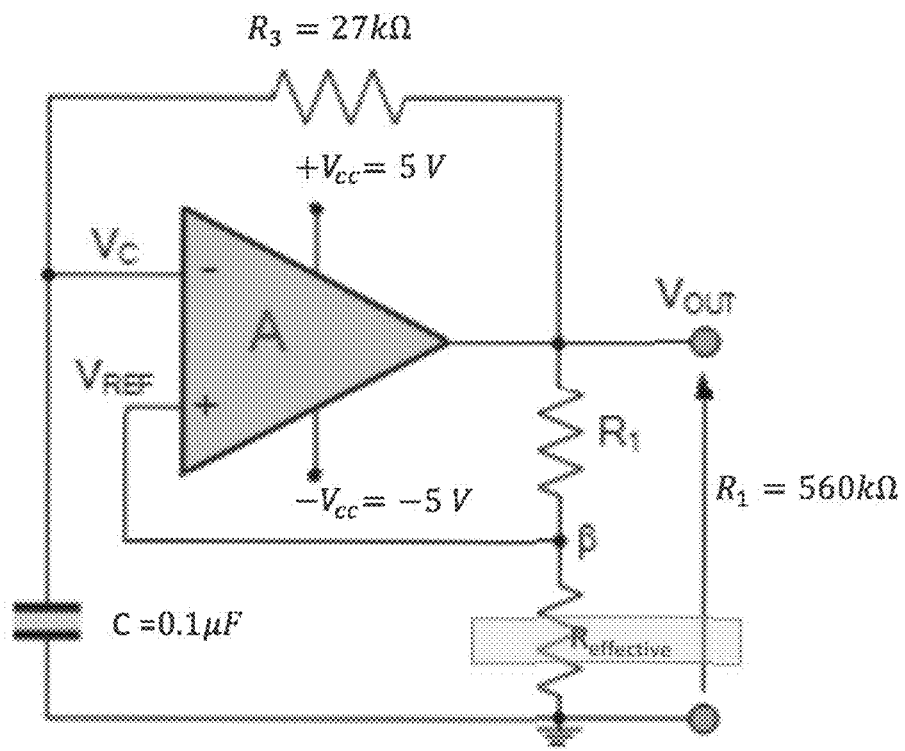
FIG. 5D illustrates an electrical schematic of an Op-amp as an astable oscillator with tissue resistance to be measured shown explicitly in the circuit.

For the purpose of this application, the resistor R2 in FIG. 5D is the effective resistance of the material (e.g. air or tissue) between the electrodes of the catheter insertion system.

The other circuit components may be chosen to affect the circuit behavior, such as to limit the current in the tissue being tested. For example, choosing a high resistor value for $R_1$ (e.g. 500 kΩ) ensures that the total amount of current introduced into the patient's body is below 10 µA.

As shown in the two examples here of a 555 timer circuit or an op-amp as an oscillator, any method known in the art may be used to determine the tissue resistance. Other suitable methods that use a time-constant of a resistor-capacitor or resistor-inductor circuit to create a dynamic response or an oscillating signal can be used to relate the time characteristics of the signal to the unknown resistance, capacitance, and/or inductance.

The microcontroller (105) is responsible for measuring the frequency of the signal produced by the timer chip, or op-amp. There are several options for conveying a detected change to the end user. One option is based on the absolute value of the measured frequency (or resistance) and the other is based on a change in measured frequency (or resistance).

When using the absolute value method, a threshold can be set (e.g., frequency <100 Hz for fatty tissue) the end user can be alerted to vein entry through output interfaces (FIG. 6) if the measured frequency value is greater than the specified cutoff. (Note that in the circuit (100) describe here, signal oscillation frequency is inversely dependent on resistance (104), so as resistance decreases, for example when the electrodes pass from fatty tissue to blood, the signal frequency increases. Other circuits in alternative embodiments can be configured so as to produce a proportional relationship between frequency and resistance. In addition, methods in which the duty cycle is measured as related to an unknown resistance, capacitance, or inductance can be utilized in some embodiments.) Setting an absolute threshold is ideal when a large separation exists between the two quantities being compared. Conversely, the absolute value method presents a problem if the two quantities being compared (e.g. blood vs. muscle) do not have a significant separation between them.

An alternative is to look for a change in baseline (or nominal or initial) frequency due to a change in resistance. This would be accomplished by setting the initial value when the needle (electrodes) first enters the tissue, for example when the measured resistance changes from air (open circuit) to skin and/or fatty tissue. The frequency observed when the electrodes are in subcutaneous (SQ) tissue can be set as the baseline and for example can be stored in memory. As the needle is advanced the user can be alerted to the change when the initial recorded frequency value rises by a certain amount (e.g. 25% increase). The algorithm within the microcontroller can monitor absolute value compared to a threshold, percentage change compared to a baseline, a combination of these changes, or other methods are possible.

The relationship between the rectangular wave frequency of the timer or oscillator circuit and the unknown resistance value ($R_{effective}$) of the tissue/fluid is described by Equation 4. Solving Equation 4 for $R_{effective}$ as shown by Equation 5 provides an expression for the unknown resistance as a function of the measured frequency. As previously noted, it is not necessary to convert the measured frequency values to resistance. This is possible because subcutaneous tissue and blood exhibit distinctive frequencies when their resistances are measured in this way that allow for differentiation between the two quantities and detection of vessel entry. The nominal output frequency of the 555 timer system is controlled by selecting the values of the resistor $R_a$ and capacitor C. Choosing a large capacitor value increases the cycle time of the system, which in turn reduces output frequency; and increasing $R_a$ increases the high time (the amount of time spent at the top of the rectangular wave) while leaving the low time (the amount of time spent at the bottom of the rectangular wave) unaffected. The respective values of C (4.7 µF) and $R_a$ (675Ω) are shown as examples that produce reasonable separation between subcutaneous tissue and blood, but many other values are feasible. In addition, in some embodiments, the system can detect the differences in resistance between subcutaneous tissue and other body fluids (e.g. peritoneal, pericardial or pleural fluid) or air (e.g. pneumothorax or air in the trachea) which has a very high resistance.

$$f = \frac{1}{T} = \frac{1.44}{(R_a + 2R_{effective})C} \tag{4}$$

$$R_{effective} = \frac{1}{2}\left(\frac{1.44}{fC} - R_a\right) \tag{5}$$

Figure 6:
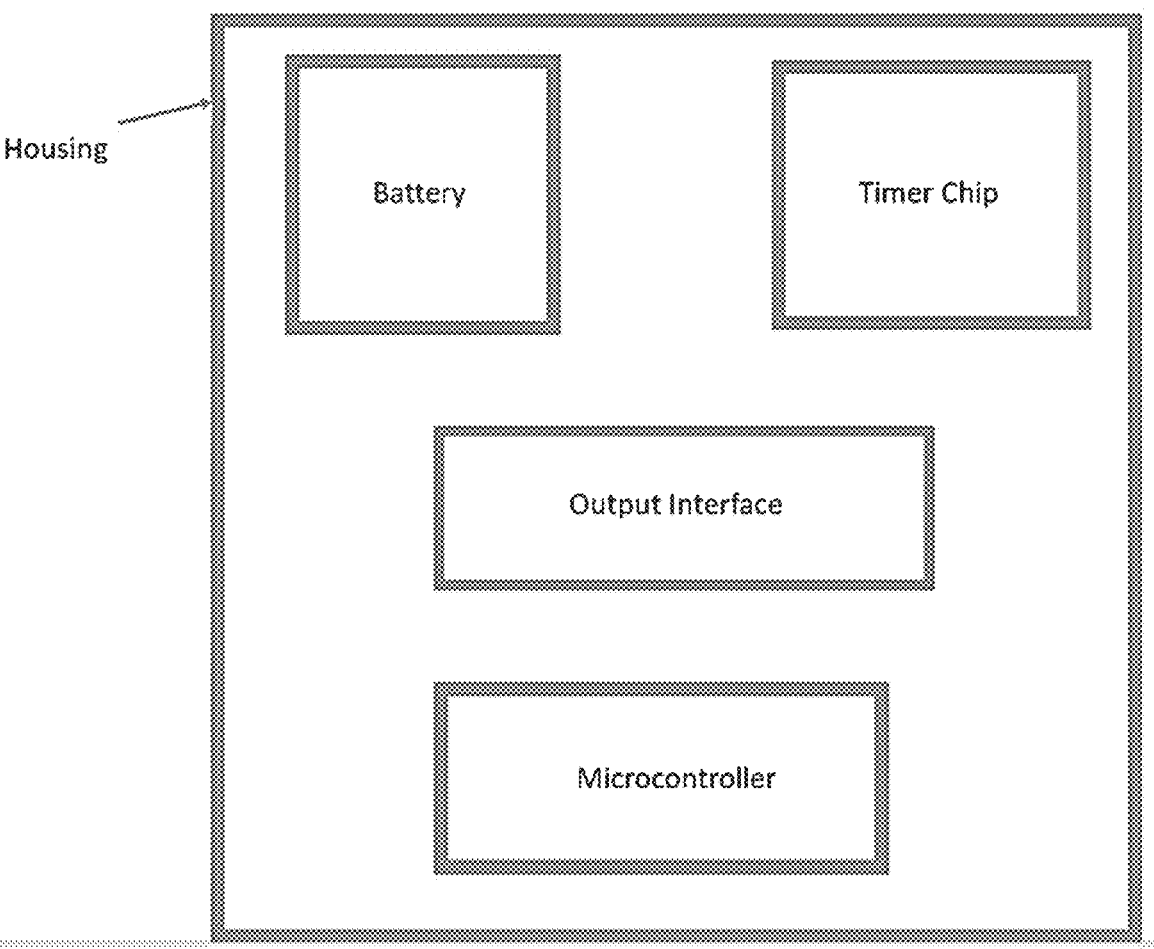
FIG. 6 is a schematic of components of the detection unit, including a battery, timer circuit, microcontroller, and output interfaces.

Shown in FIG. 6 is a schematic of components of one exemplary detection unit. The detection unit can comprise a battery to power the device, timer circuit (or alternative oscillatory component or circuit), microcontroller (frequency measurement and interface control), and output interface(s) such as speaker, LED or other light output, vibratory or other tactile interface, and/or LCD or other alpha numeric or graphical display. The components of the detection unit, some of which may be mounted on a printed circuit board, are packaged within a small housing (e.g. 2 in×2 in) which allow the overall system to be portable making it easier to use.

In addition to the components shown in FIG. 6, it is possible to add a radio component to the detection unit (for example, RF. NFC, Bluetooth, WiFi, or other suitable component) that enables the system to communicate wirelessly to a mobile device (e.g. a cell phone) or a network or a computer such that the information (measured frequencies and/or resistance values) can be transferred to such devices, computers, and/or networks. Software applications can execute on the devices (e.g. an app on a mobile phone or computer or software on a server) that can receive, analyze, and/or store the data (for example in a database in a server). In such cases the human interface (e.g. lights, sounds, vibrations, etc.) can be presented on the mobile device or on some other device connected to a computer in addition to or in place of the output interface(s) of the detection unit. A software application on a mobile device or computer can be configured to enable the hardware (electrode system, detection unit, or a combination) to operate the same or differently for medical procedures other than pIV placement. For example placement of pleural, pericardial or peritoneal catheters. In such a scenario, for example in which a cell phone is wirelessly connected to the detection unit, the user could select in the app what procedure is to be executed, and information could be transferred from the phone to the detection unit to establish operating methods in the microcontroller. For example, one or more parameters could be passed to the microcontroller to indicate that pIV is the procedure of interest, so associated frequency or resistance values can be measured or passed back to the mobile device or computer or network to be analyzed, stored (for example in a database on the network or in the mobile device or computer) or to be used to alert the user. The information transferred from the detection unit could be measurement of frequency or resistance at specific times (e.g., periodically) or based on events (e.g., changes in frequency or alerts that a frequency threshold has been crossed), or it could be alerts that certain events have occurred. Alternatively, data from the detection unit could be streamed in real time to the mobile device or computer or network so that it may be analyzed in real time to be used immediately by the user or be stored for future use.

An alternative to using the detection unit as depicted in FIG. 3 is to place the circuit into the catheter system itself. In this case it can be referred to as a detection circuit instead of a detection unit. The detection circuit can be miniaturized (including the components of FIG. 6) onto a printed circuit board or as a system-on-a-chip such that it can be included as an integral part of the catheter system (200) of FIG. 3, thereby eliminating the need for a separate detection unit shown in FIG. 3. In such case there may be a radio included for wireless communication with a detection unit, or a mobile device as described above, or the circuit could be connected directly to the mobile device or computer through wires. When wired directly, certain functions can be carried out by the mobile device or computer thereby allowing elimination of that related component from the detection circuit, for example eliminating the microcontroller in the detection circuit (and carrying out the analysis and control on the mobile device), or eliminating the battery (whereby the detection circuit is powered from the mobile device through wires), or eliminating the timer circuit (in which case timing or oscillator generator or similar function is executed on the mobile device or computer), or eliminating the output interface (and using the user interfaces on the mobile device to relay information and alerts to the user), or eliminating combinations of these components.

Another alternative to using a timer circuit or another oscillating circuit for measuring the unknown tissue/fluid resistance is to utilize a Wheatstone bridge and alternating current (AC). Unlike DC bridges, where the resistance can be directly measured, AC bridges measure the impedance. Equation 6 displays a general expression for impedance, where R is the real component and jX is the imaginary component.

$$Z=R+jX \qquad (6)$$

An AC bridge is used instead of DC in order to negate the effect of polarization. Applying a direct current to a liquid solution causes an accumulation of ions near the surface of the electrodes which leads to the polarization of the measurement electrodes and thus erroneous results. Applying alternating current forces the ions to continuously migrate from one electrode to the other thus effectively negating the effect of polarization.

Figures 7, 8:
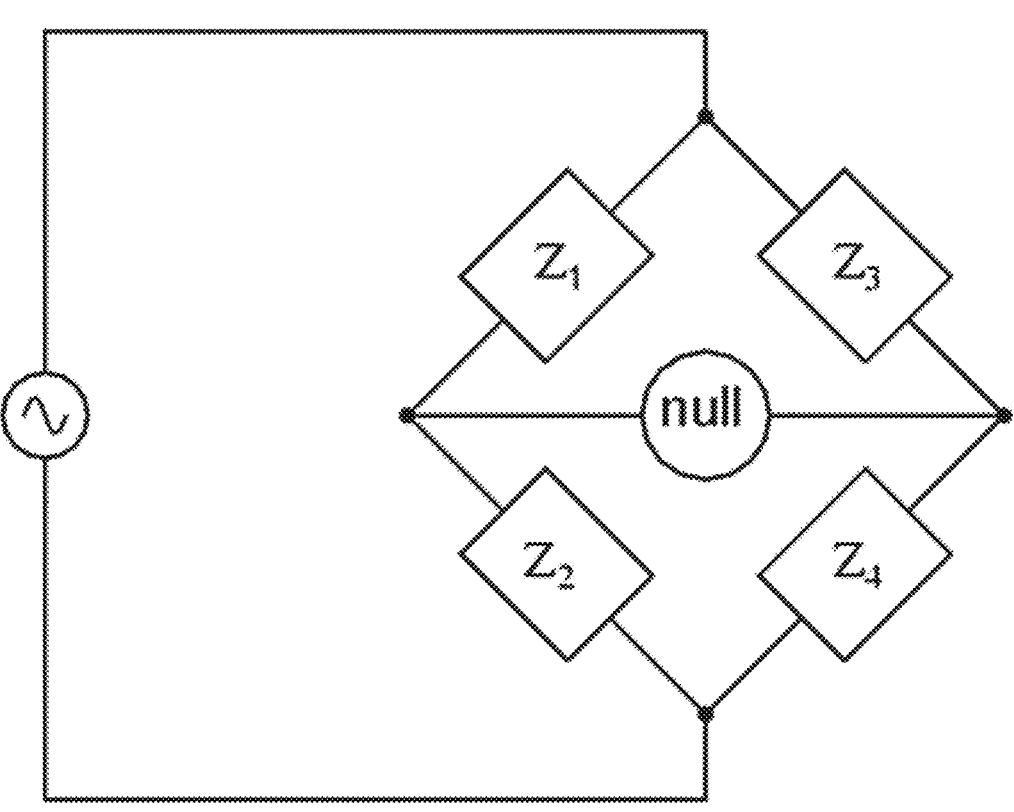
FIG. 7 is a schematic of a balanced AC Wheatstone bridge, where $Z_1$, $Z_2$. $Z_3$, $Z_4$ are the impedances, and "null" indicates an output bridge voltage in the balance condition.
FIG. 8 is a schematic of a Wheatstone bridge, with impedances shown as pure resistors, in an arbitrary unbalanced condition, where Vb is the unbalanced voltage. Vin is the input voltage Ra, Rb, and Rc are known resistance components, and Rx is the unknown component.

Shown in FIG. 7 is a schematic of a balanced AC Wheatstone bridge, where given an arbitrary AC voltage $Z_1$, $Z_2, Z_3, Z_4$ are the resulting impedances, and "null" indicates an output bridge voltage in the balance condition. The operation of an AC Wheatstone bridge is described here to clarify how it is used to measure tissue/fluid resistance in the present invention. The bridge circuit works as a voltage divider when connected to a power source. A specific input voltage will result in a corresponding output voltage. A balanced condition occurs when the voltage difference and current flow between the two legs is zero. A balanced condition results in the output bridge voltage being negligible or "null" (FIG. 7). This allows for the determination of the balance condition (Equation 7). The relationship states that in order for the bridge to balance, the ratio of the impedances of any two adjacent arms must equal the ratio of the impedances of the remaining two arms.

$$\frac{Z_1}{Z_2} = \frac{Z_3}{Z_4} \qquad (7)$$

FIG. 8 shows the Schematic of a Wheatstone bridge, with impedances shown as pure resistors, in an arbitrary unbalanced condition. For a given input the output of the bridge will reflect the extent of the unbalance as, $V_b$ is the unbalanced voltage, $V_{in}$ is the input voltage $R_a$, $R_b$, and $R_c$ are known resistance components, and Rx is the unknown component (FIG. 8). In the present application, the imaginary component of the bridge is neglected and only the real portion considered since the fluid/tissue resistance is the dominant effect. Other bridge configurations can be included is different embodiments, for example using "dummy" resistors to account for unwanted noise and errors.

Applying the voltage divider relationship (Equation 8) an expression is obtained which allows for the determination of the unbalanced voltage for a given input (Equation 9). The unbalanced voltage in the bridge circuit is measured by a microcontroller (e.g., ATmega328p) which measures the unbalanced voltage and alerts the user to vessel entry through an audible tone or other interfaces (FIG. 9).

$$v_b = \frac{R_b}{R_a + R_b} v_{in} \qquad (8)$$

$$v_b = v_{in}\left(\frac{R_x}{R_x + R_c} - \frac{R_b}{R_b + R_a}\right) \qquad (9)$$

Figure 9:
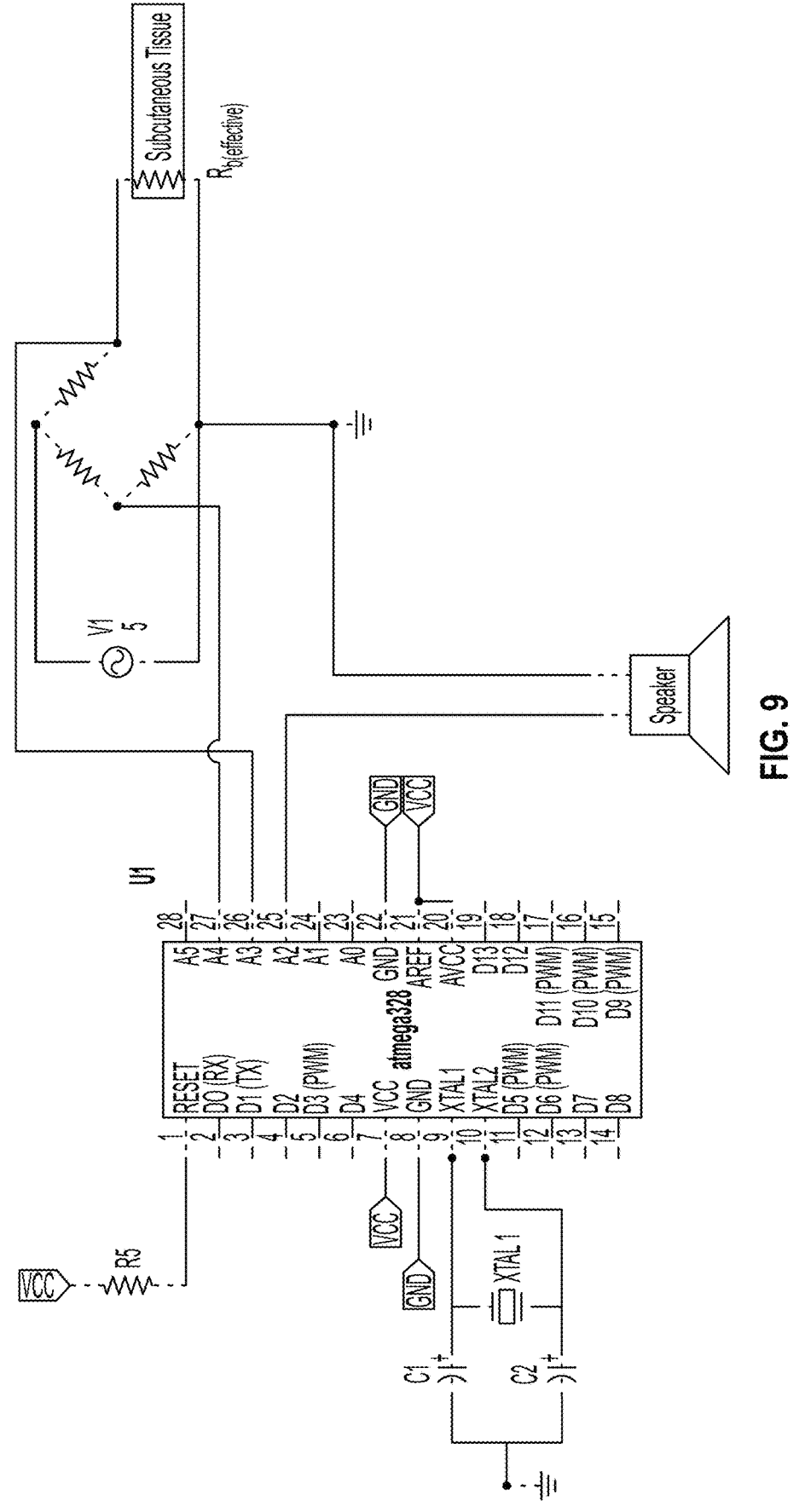
FIG. 9 is a circuit diagram of the Wheatstone bridge where Rx is made up of the tissue resistance between the needle and guidewire ($R_{effective}$). The value of the unbalanced voltage is sent to a microcontroller, which alerts the operator to a change.

In the present application, the tissue/fluid being measured will take the place of the resistance value $R_x$, as depicted in FIG. 9. Although only subcutaneous tissue is shown in the figure, it should be noted that the needle encounters other materials such as blood and muscle during use. In the disclosed systems, the unknown tissue/fluid resistance can be determined by using Equation 7 which in turn allows for the differentiation between subcutaneous tissue and blood. It is not necessary to convert the measured unbalanced bridge voltage values to their corresponding resistance values. This is possible because subcutaneous tissue and blood have distinct unbalanced voltages that can be measured using a microcontroller as mentioned above.

Figure 10:
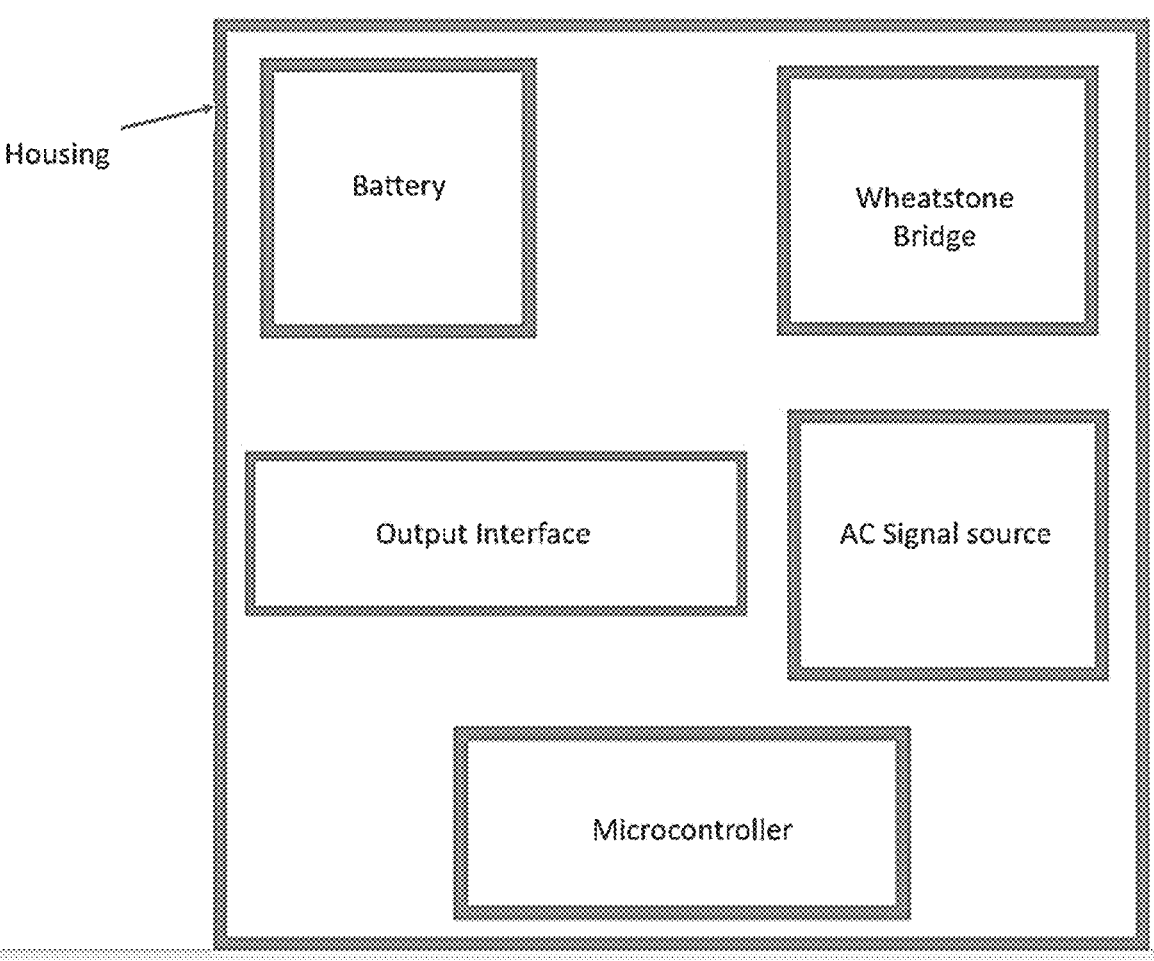
FIG. 10 is a schematic of components of the detection unit, including a battery, an AC signal source, Wheatstone bridge circuit, microcontroller, and output interface(s).

Shown in FIG. 10 is a schematic of components of the alternate detection unit. Some disclosed detection units can comprise a DC battery source to power the device, Wheatstone bridge circuit, an AC signal source for the Wheatstone bridge, a microcontroller (unbalanced voltage measurement and interface control), and output interface(s) such as such as speaker, LED or other light output, vibratory or other tactile interface, and/or LCD or other alpha numeric or graphical display which will notify the user of vein entry. The components of the detection unit, some of which may be mounted on a printed circuit board, are packaged within a small housing (e.g. 2 in×2 in) which will allow the overall system to be portable making it easy to use.

$$R_x = \frac{\left(R_b R_c + \frac{V_b}{V_{in}}(R_a + R_b)\right)}{\left(R_a - \frac{V_b}{V_{in}}(R_a + R_b)\right)} \qquad (10)$$

Figure 11:
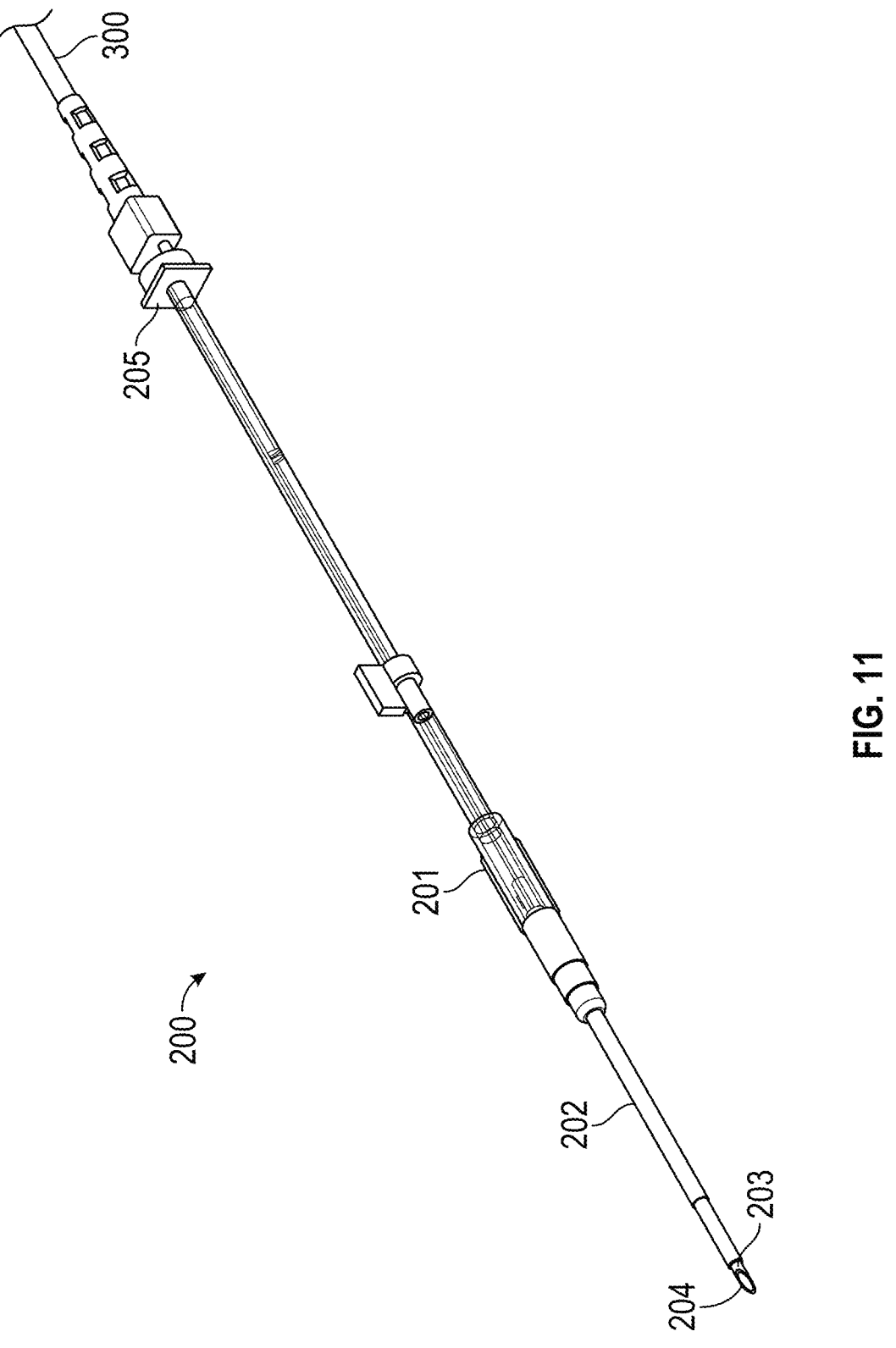
FIG. 11 shows an exemplary needle and wire disposable catheter unit.
Figure 12A:
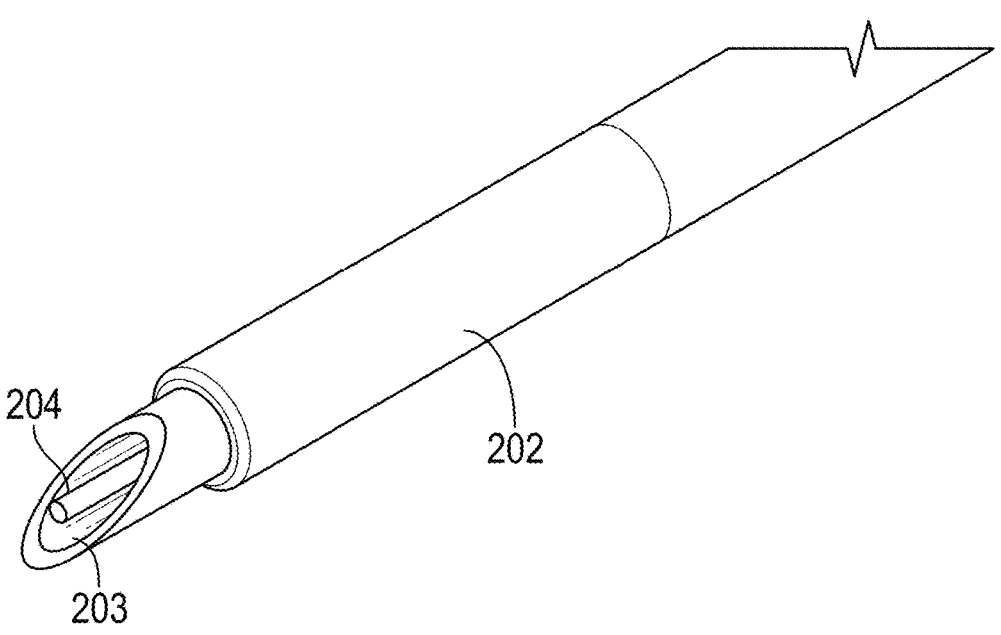
FIGS. 12A and 12B are detailed views of the needle and wire disposable catheter unit design.
Figure 12B:
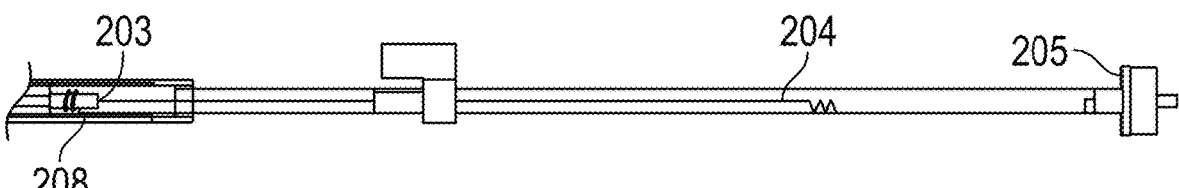

An exemplary disposable catheter unit (200) of the disclosed system is shown in FIG. 3 and further illustrated in FIGS. 11 and 12A-12B. The catheter unit (200) can include a needle (201), a removable catheter (202), needle housing acting as the first electrode (203), guidewire acting as the second electrode (204) electrical connector (205). The electrical connector attaches to a mating connector from a non-disposable cable (300), as also shown in FIG. 3. FIGS. 12A and 12B show detailed close-up views of the disposable catheter unit. An integrated Seldinger catheter is shown in FIG. 13 for comparison.

The disposable catheter unit can comprise a pIV in which a sterile guide wire inside a plastic sheath is fitted. The plastic sheath provides a pathway for guidewire advancement, and it also allows for additional guide wire length by coiling the guidewire inside the tubing (described below). In the disclosed systems (e.g., FIG. 12A) the guidewire can lie inside the IV needle and its free end can be located just under the bevel. The wire can be smaller than the inner diameter of the needle (for example, a 0.0201 inch wire (24 gauge) for a 0.063-inch (14 gauge) needle, or 0.01-inch wire (30 gauge) for a 0.033 inch (18 gauge) needle). The inside surface of the needle can be coated with an insulating material (for example silicone, or polyurethane) leaving only the outer portion of the needle exposed, which acts as the first electrode (203). The uncoated guide wire inside the needle itself acts as a second electrode (204) (FIG. 12A). The insulated coating inside the needle prevents a short-circuit to occur between the two electrodes. In some embodiments, both of the electrodes can be connected to an electrical connector (205) and the catheter assembly can be connected to the detection unit by cable (300) that is attached where the operator holds the unit as shown in FIG. 11.

Figures 13, 14A:
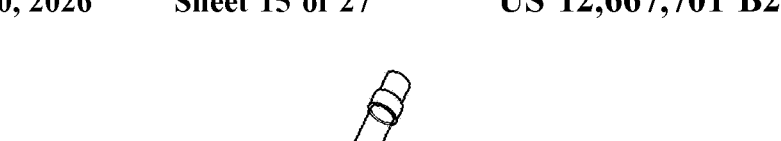
FIG. 13 shows an integrated Seldinger Arterial Catheter. A sterile guidewire within a plastic sheath fits on top of a pIV needle/catheter.
FIGS. 14A-14D are needle and wire catheter designs during various stages of use.
Figure 14B:
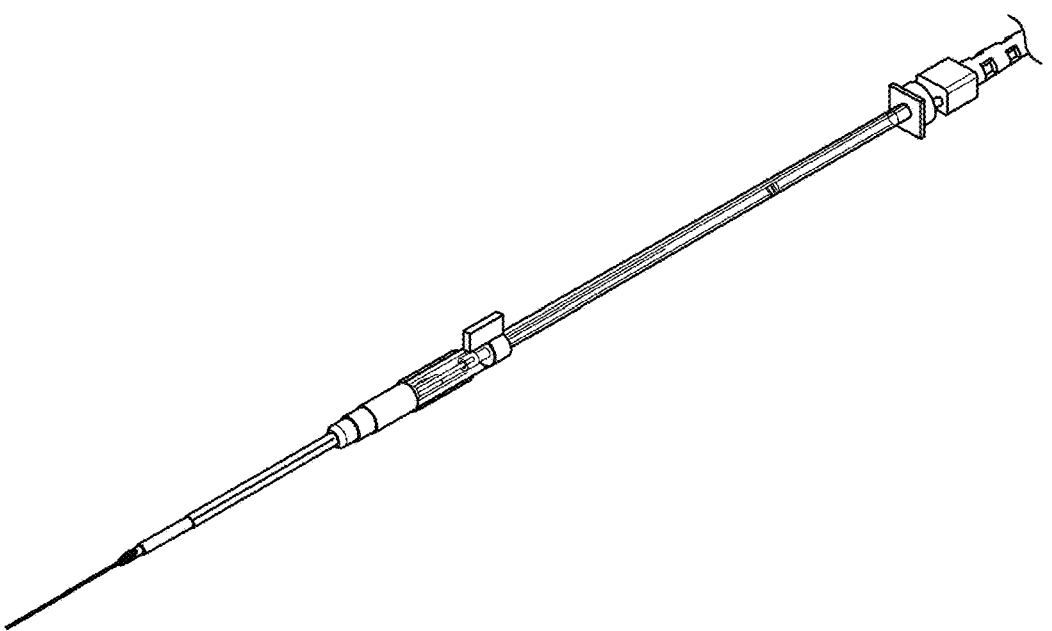
Figure 14C:
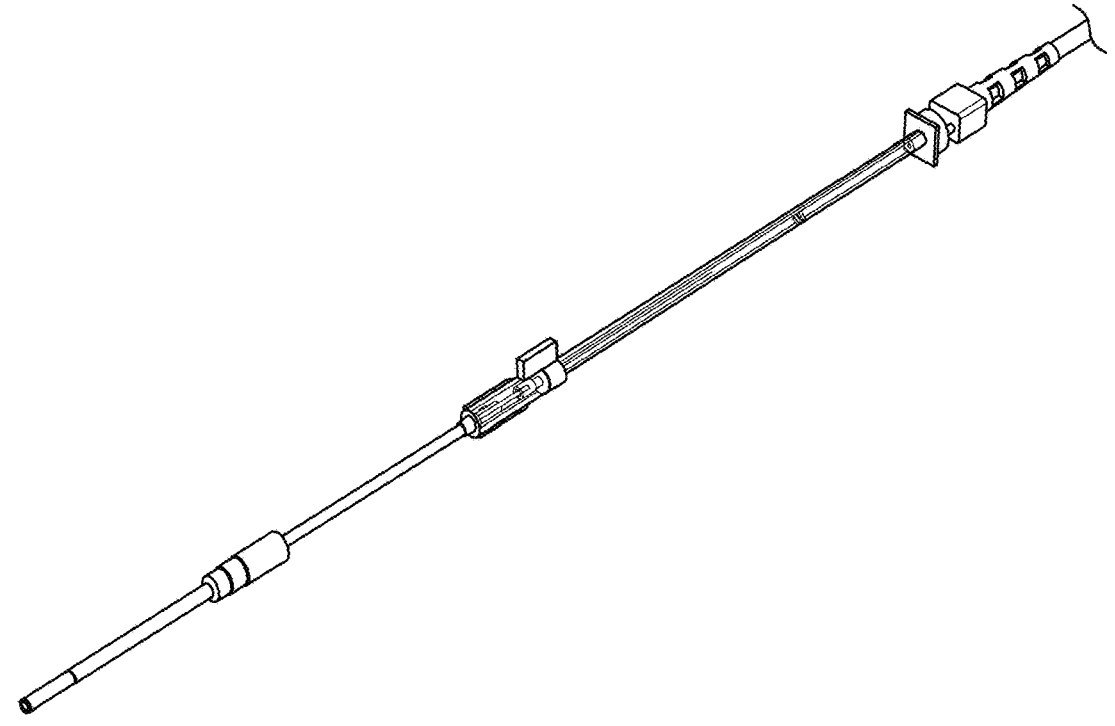
Figure 14D:
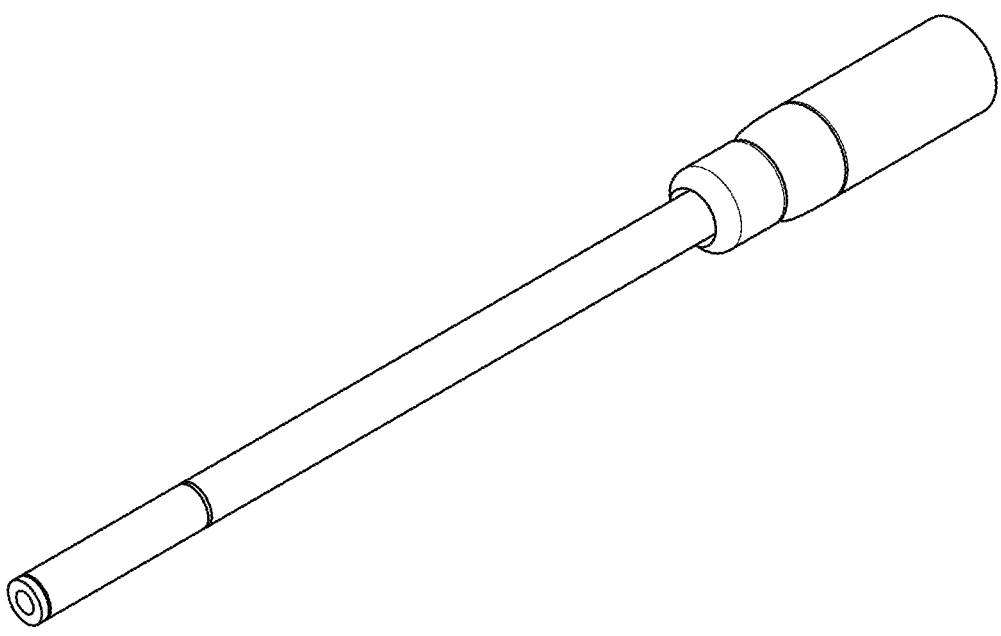

FIGS. 14A-14D show an exemplary modified catheter unit during various stages of use. As mentioned above, the guide wire sits just under the bevel and it serves as the second electrode (204) while the needle housing serves as the first electrode (203) (FIG. 14A). In the current design, a wire (208) is attached to the needle housing in order to provide an electrical signal to the detection unit via connector (205). Furthermore, additional guidewire length is provided by coiling the wire inside the plastic tubing (or otherwise looping or arranging excess wire in other paths) as shown in (FIG. 12B). Doing so allows for the deployment of the guidewire while maintaining connection with the electrical connector as shown in FIG. 14B in the catheter deployment process. Once the catheter has been advanced into the vein, the needle assembly is withdrawn (FIG. 14C) and disconnected from the cable (300) of the detection unit making the entire assembly disposable after single use.

Figure 15:
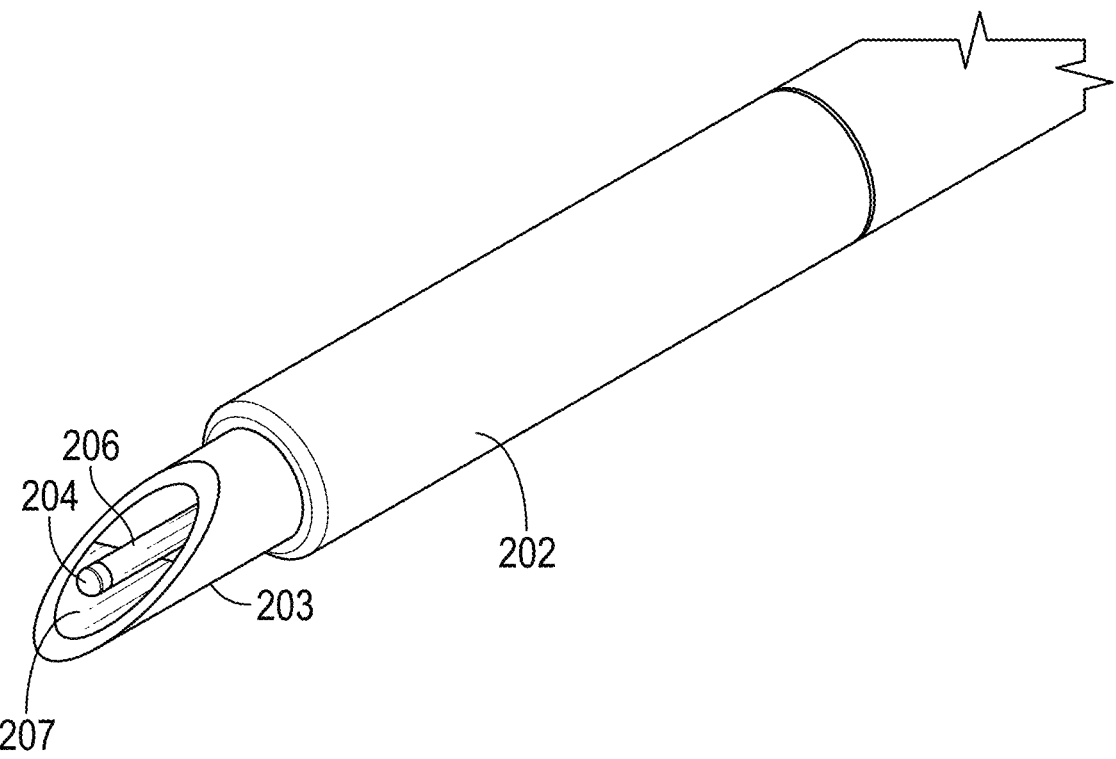
FIG. 15 shows another exemplary needle and wire configuration, where the guidewire which serves as the second electrode is coated with an insulating material except at the tip. The needle is coated at the tip while the remaining surface is left bare allowing for the housing to act as the first electrode.

An alternative needle and wire embodiment is shown in FIG. 15. The layout of the two electrodes is similar the other embodiment disclosed herein. In this embodiment, the guidewire, which serves as the second electrode (204), is coated with an insulating material (206) (e.g. silicone or polyurethane) except at the tip which is left bare. The needle housing, which acts as the first electrode (203), may be coated with an insulating material at the tip (207), while the remaining inside surface is left bare (FIG. 15). The insulating coating on the guidewire, and at the tip of the needle prevents a short circuit from occurring between the two electrodes.

Figure 16A:
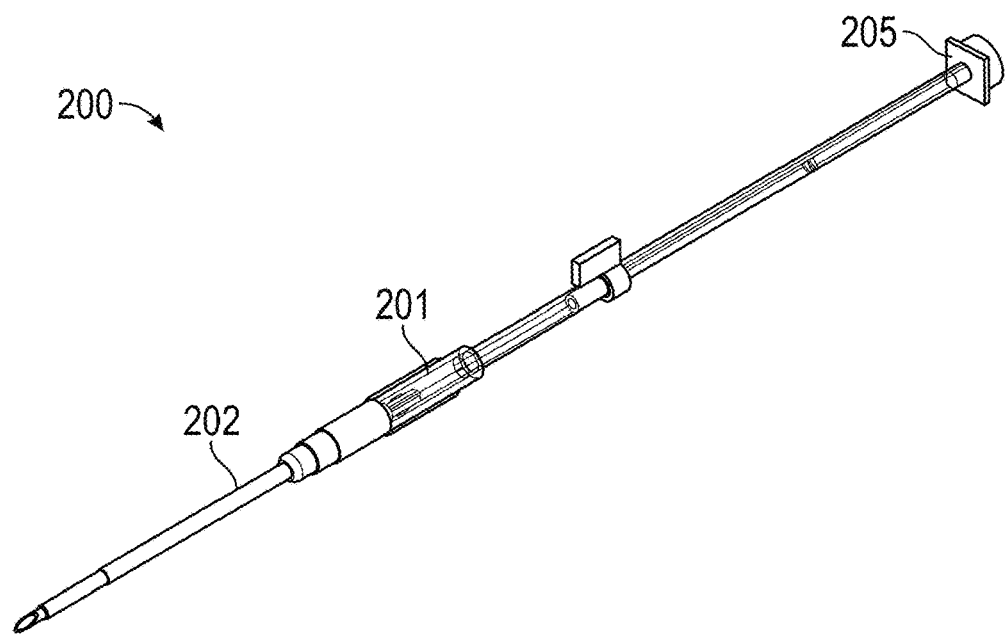
FIGS. 16A-16C illustrate an exemplary two wire disposable catheter configuration.
Figure 16B:
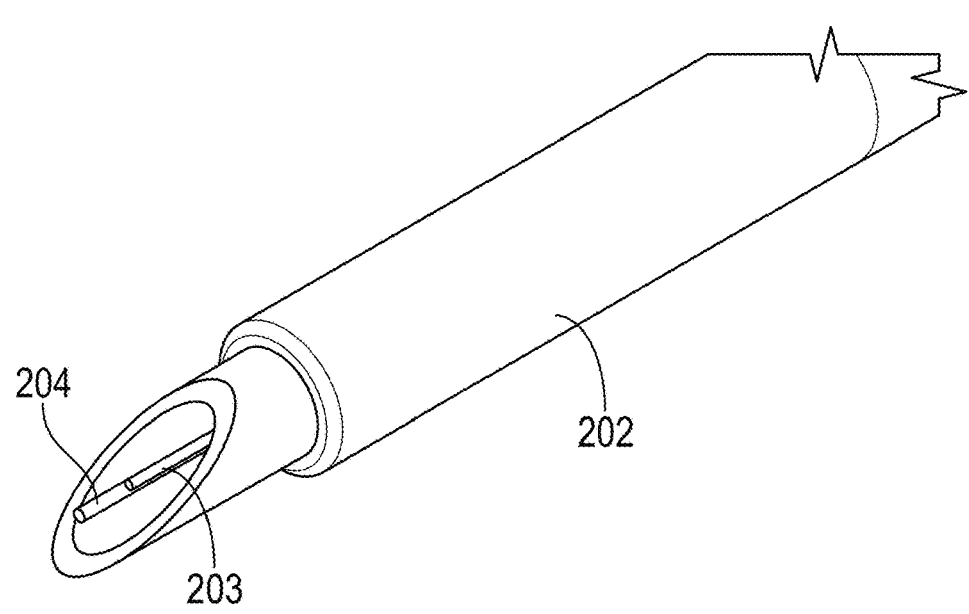
Figure 16C:
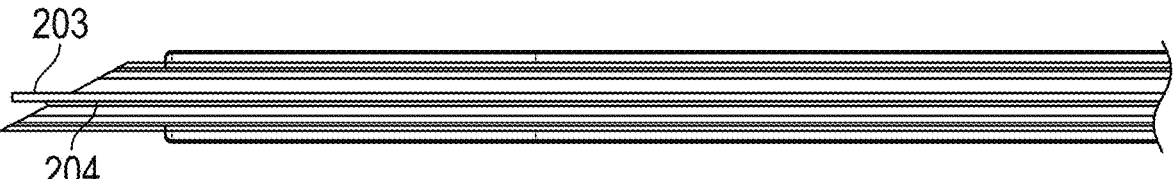

Other exemplary disposable catheter units can comprise a modification to the guide wire, where two staggered wires inside of the needle act as the two individual electrodes while the plastic catheter is fitted over the needle. FIGS. 16A-16C illustrate an exemplary two-wire disposable catheter design. FIG. 16A shows a schematic of a two-wire disposable catheter unit. FIG. 16B, displays an enlarged view of the wire arrangement where each wire has an exposed end that serve as the first and second electrodes. In this embodiment, both of the electrodes lie inside the needle and under the bevel. The first electrode (203) is staggered or otherwise separated from the second electrode to prevent short circuit (FIG. 16C). The illustrated two-wire combination provides one alternative version of the guide wire, although other arrangements are possible (e.g., both wires housed inside a single insulated sheath, or the two wires separated by a small distance, or the two wires inter-wrapped).

The wires can be insulated to prevent a short circuit between them. In addition, the inside of the needle may be coated with an insulating material (for example silicone, or polyurethane) preventing a short circuit between the wires and the needle should they come into contact. The two wires inside are smaller than the inner diameter of the needle (for example a 0.0201 inch wire (24 gauge) for a 0.063-inch (14 gauge) needle, or 0.01-inch wire (30 gauge) for a 0.033-inch (18 gauge) needle) allowing both to fit freely inside of the needle housing. Both wires are connected to the electrical connector (205) and the catheter assembly is connected to the detection unit by cable (300) that is attached where the operator holds the unit (FIG. 16A). During various stages of use, (FIGS. 14A-14D) additional guidewire length is provided by coiling both the wires inside the plastic tubing as shown above in FIG. 12D. This allows for the end user to maintain electrical connection while the guidewire is advanced. Once the catheter has been advanced into the vein, the needle assembly is withdrawn (FIG. 14C) and disconnected from the cable (300) of the detection unit making the entire assembly disposable after single use.

Three sets of tests were carried out involving the disposable catheter embodiments and the 555 timer detection unit disclosed herein. The first test involved inserting two electrodes (two separate wires, similar to the embodiments described above but without the wires being housed inside a needle) into various materials to measure the resistance. Materials tested were pork fat, pork shoulder (muscle) and Plasma-Lyte A (a commercially available liquid that has electrical properties similar to blood). In the second test, the needle- and-wire disposable catheter design was inserted into each of the individual materials as in the first tests (pork fat, pork shoulder (muscle), and Plasma-Lyte A) in order to determine feasibility of discerning between key materials. Although subcutaneous tissue behaves as fat, muscle was tested in order to account for the extreme cases such as a "blown vein" which occurs when the user advances the needle through the vein into surrounding tissue. If muscle is a tissue state indicated by the device, then the system can notify the user that the needle has advanced beyond the vein. The final test consisted of multiple layers where the needle-and-wire disposable catheter assembly traveled through fat prior to entering the Plasma-Lyte. A channel in order to simulate the real-world scenario. In all tests, the oscillator circuit design was used to determine measured resistance.

Figure 17A:
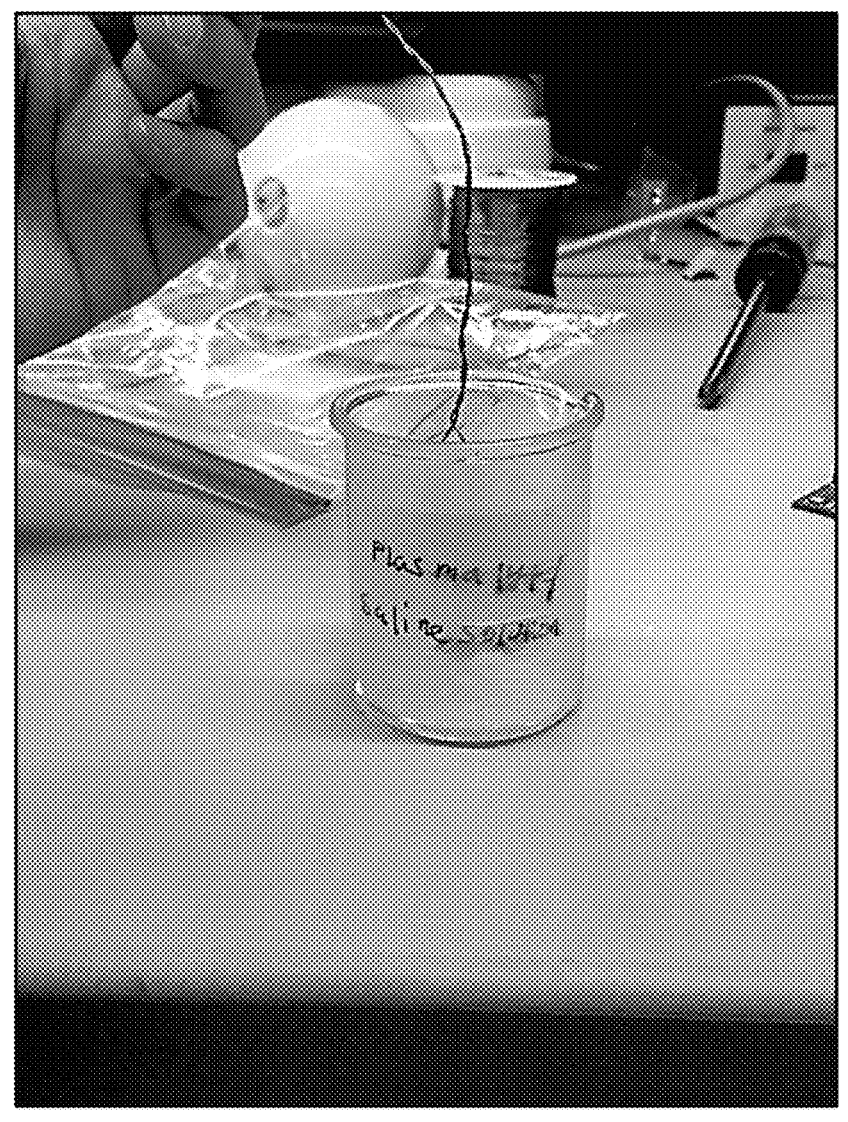
FIGS. 17A-17C show test setups using two wires.
Figure 17B:
Figure 17C:
Figure 18:
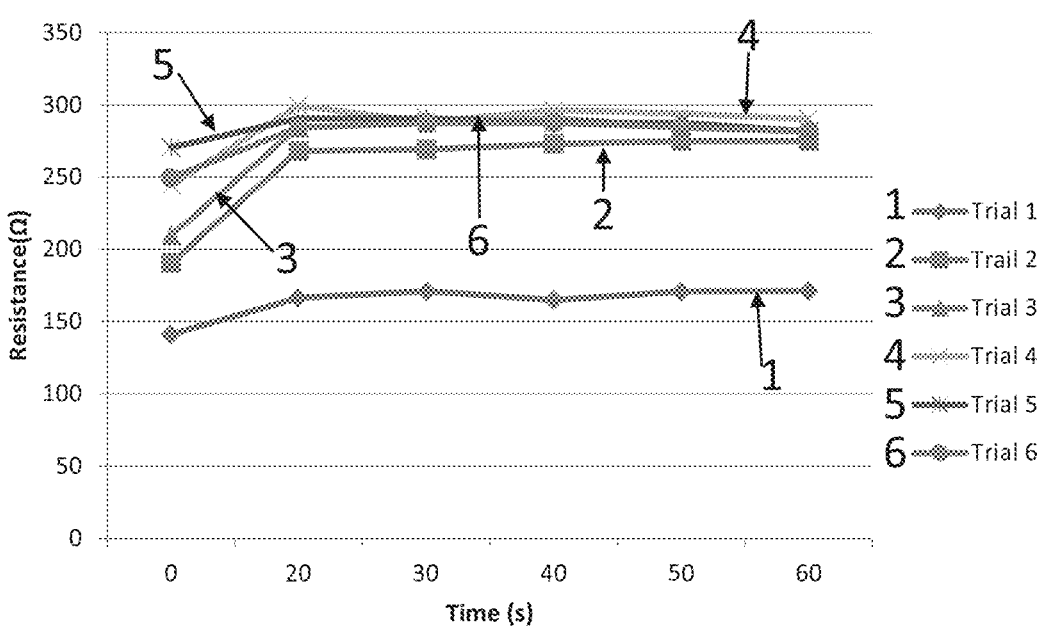
FIG. 18 is a plot of Plasma-Lyte A resistance vs. time through six trials using two wire electrodes.
Figure 19:
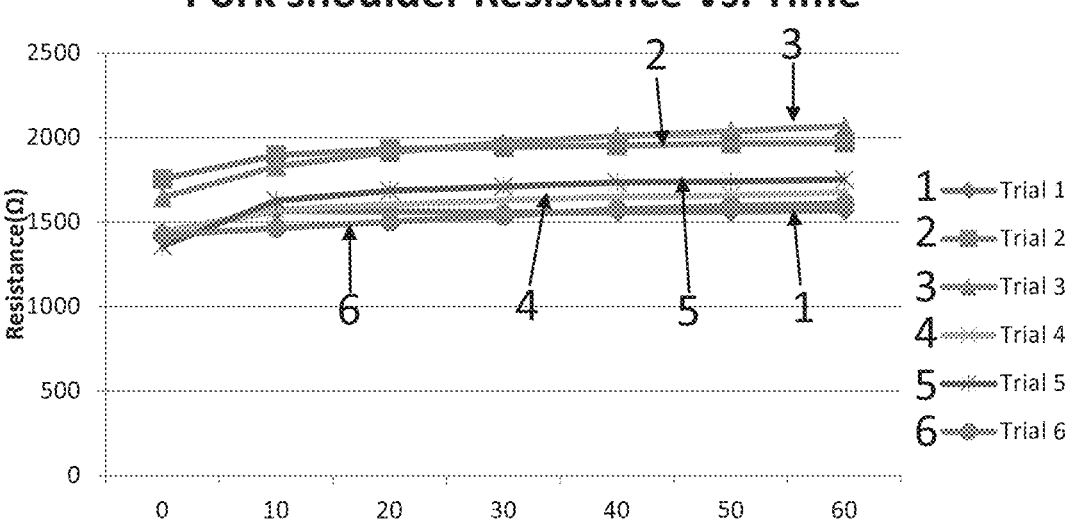
FIG. 19 is a plot of pork shoulder resistance vs. time through six trials using two wire electrodes.
Figure 20:
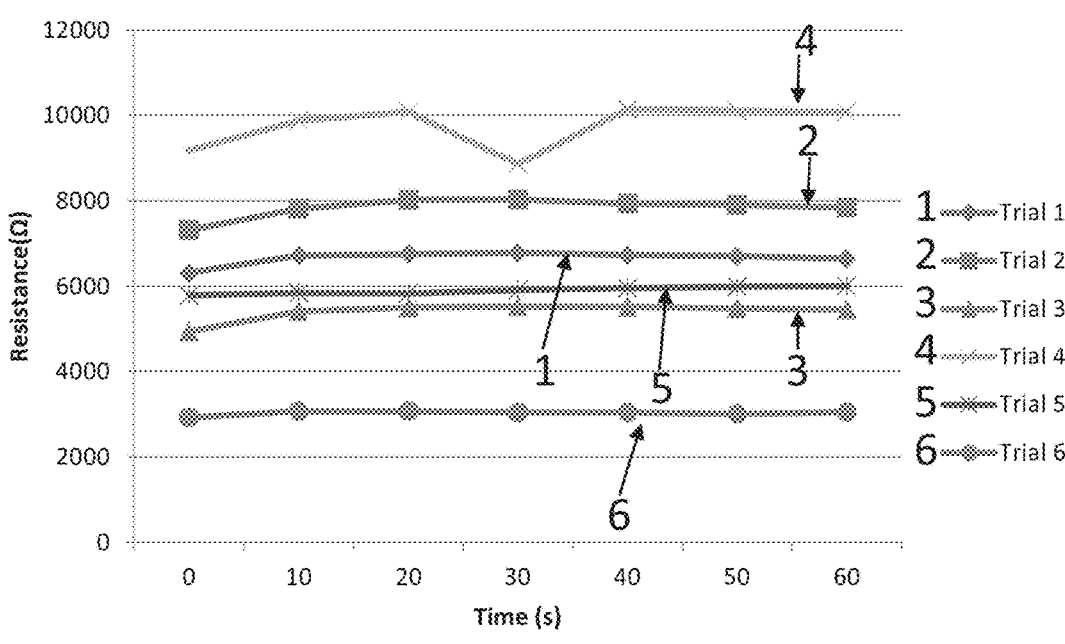
FIG. 20 is a plot of pork fat resistance vs. time through six trials using two wire electrodes.

FIGS. 17A-17C shows example photos of the first tests in the various materials, which served as proof of concept tests to validate the full disposable catheter designs. During the first test, wires that made up the two electrodes were submerged in Plasma-Lyte A solution for one minute and the frequency output by the oscillator circuit was collected every ten seconds. Subsequently, the wires were used to puncture pork fat and muscle for one minute, and the output frequency was collected every ten seconds. On average, catheter placement takes about 10-15 seconds, thus making an accurate and rapid detection (e.g. less than 500 ms) of the frequency values important. In each trial, the data was collected for one minute in order to obtain the steady state values of each individual material tested. The tests were repeated for a total of six trials in order to assess consistency and repeatability of the data in each individual material. In between each trial, the electrodes were cleaned in order to avoid erroneous results from contaminated electrodes. The recorded frequency values were converted to resistance using Equation 2 described above. FIGS. 18-20 display the results of these tests.

Figure 21:
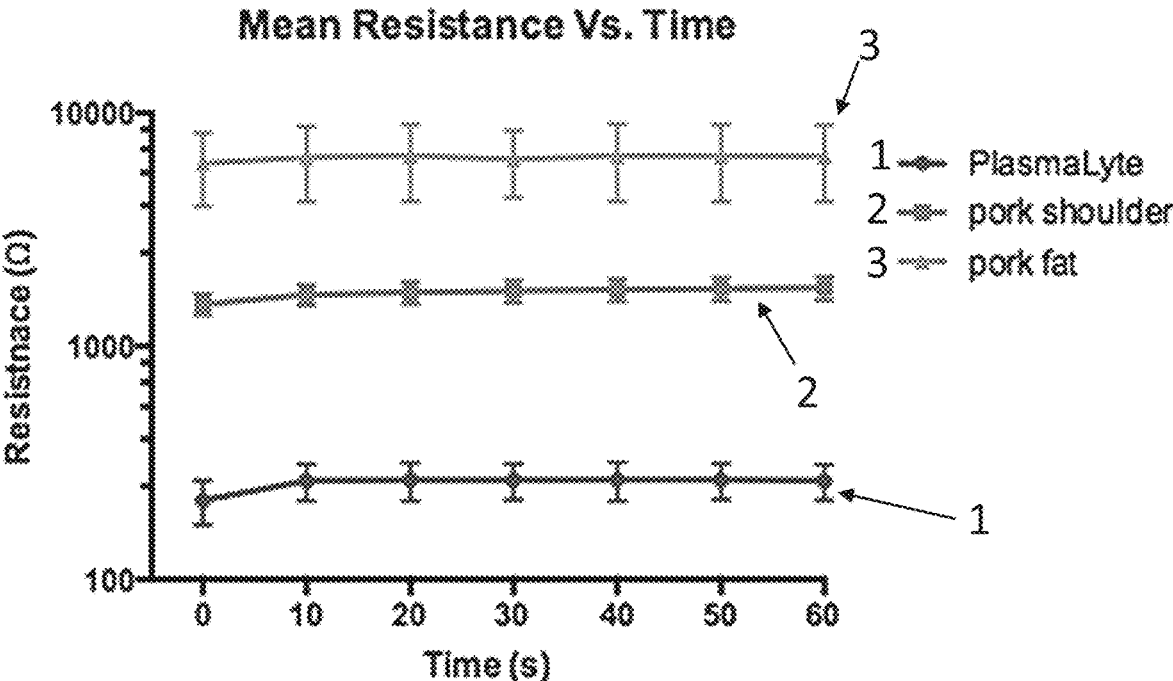
FIG. 21 shows mean and standard deviations for the resulting resistance measurements of Plasma-Lyte A vs. muscle vs. fat using two wire electrodes.

In FIG. 18, the graph shows that the resistance value of the Plasma-Lyte A solution starts around 140-275Ω and it reaches steady state of around 300Ω in five out of the six trials. In FIG. 19 the graph shows that the resistance value of the muscle (pork shoulder) had an initial value of approximately 1400-1800Ω and the resistance values reached equilibrium between 1600-2200Ω during the six trials. FIG. 20 displays the plot of the pork fat resistance vs. time. From the figure, it can be noted that resistance value of the fat had an initial value of approximately 3000-9100Ω and the resistance values reached equilibrium between 3000-1000052 during the six trials. Finally, FIG. 21 displays a plot of the mean and standard deviation of the resulting resistance measurements of Plasma-Lyte A vs. muscle vs. fat. From the plot, it can be seen that there is a large magnitude of difference between the measured resistances of pork fat, muscle (pork shoulder), and Plasma-Lyte A and the recorded resistance values are stable for the duration of the tests. These results indicate that the method is feasible for discerning between key materials encountered by a needle when a catheter is placed.

Figure 23:
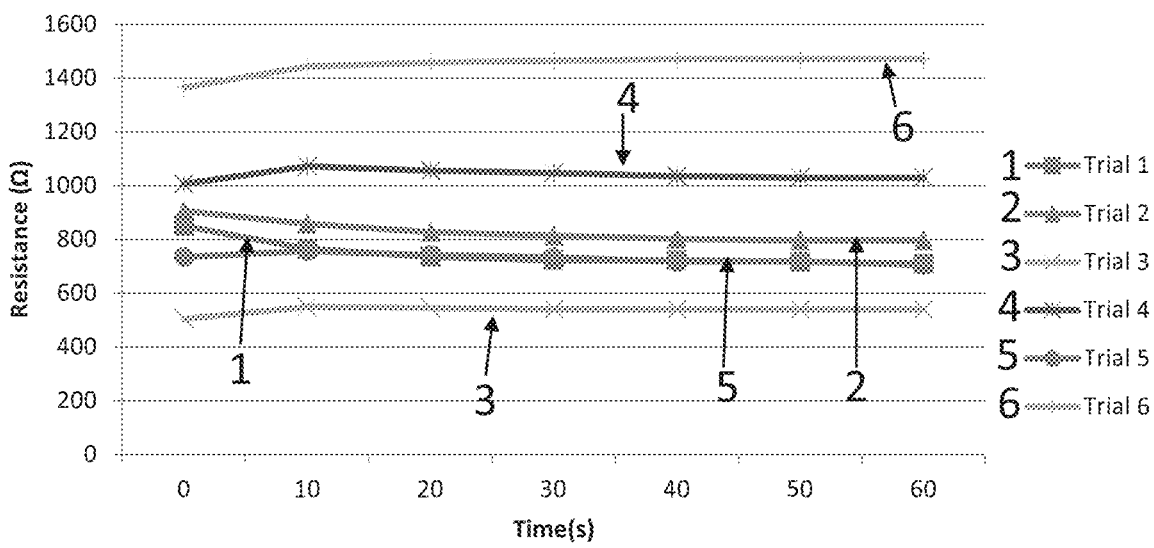
FIG. 23 is a plot of pork shoulder resistance vs. time through six trials using the needle- and-wire design.
Figure 24:
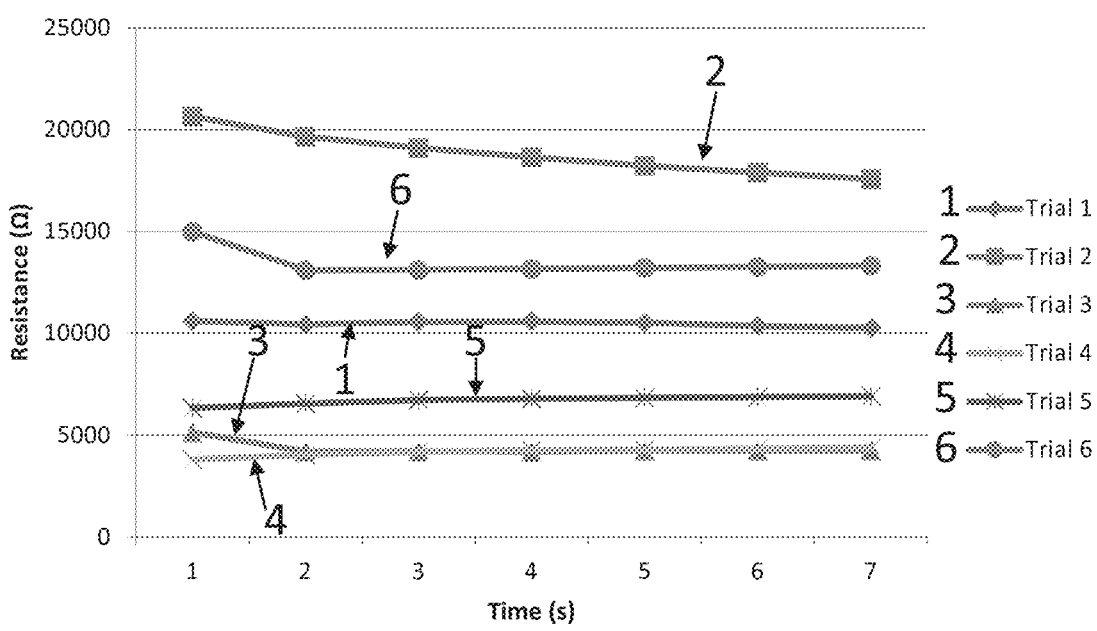
FIG. 24 is a plot of pork fat resistance vs. time through six trials using the needle- and-wire design.

The second test was performed with the same materials shown in FIGS. 17A-17C but with the needle- and-wire disposable catheter design. For the second test, the same testing procedure was followed as previously described. The results are shown in FIGS. 22-24.

Figure 22:
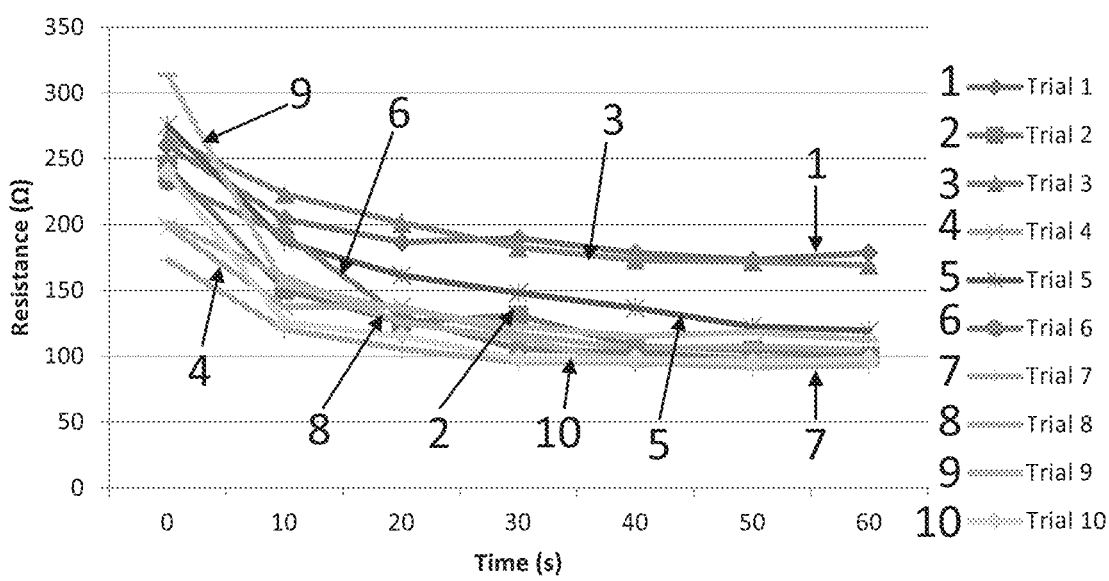
FIG. 22 is a plot of Plasma-Lyte A resistance vs. time through six trials using the needle- and -wire design.

In FIG. 22, the graph shows that the resistance value of the Plasma-Lyte A solution starts around 173-325Ω and it reaches a steady state value between 100-170Ω in ten trials. In FIG. 23 the graph shows that the resistance value of the muscle (pork shoulder) had an initial value of approximately 500-1400Ω and the resistance values reached equilibrium between 540-1500Ω during the six trials. FIG. 24 displays the plot of the pork fat resistance vs. time. From the figure, it can be noted that resistance value of the fat had an initial value of approximately 2900-9100Ω and the resistance values reached equilibrium between 3000-10000Ω during the six trials. From the plots, it can be seen that there is a large magnitude of difference between the resistances of fat, muscle, and Plasma-Lyte A and the recorded resistance values are stable for the needle- and-wire disposable catheter design. These results indicate that the method is feasible for discerning between key materials encountered by a needle when a catheter is placed.

Figure 25A:
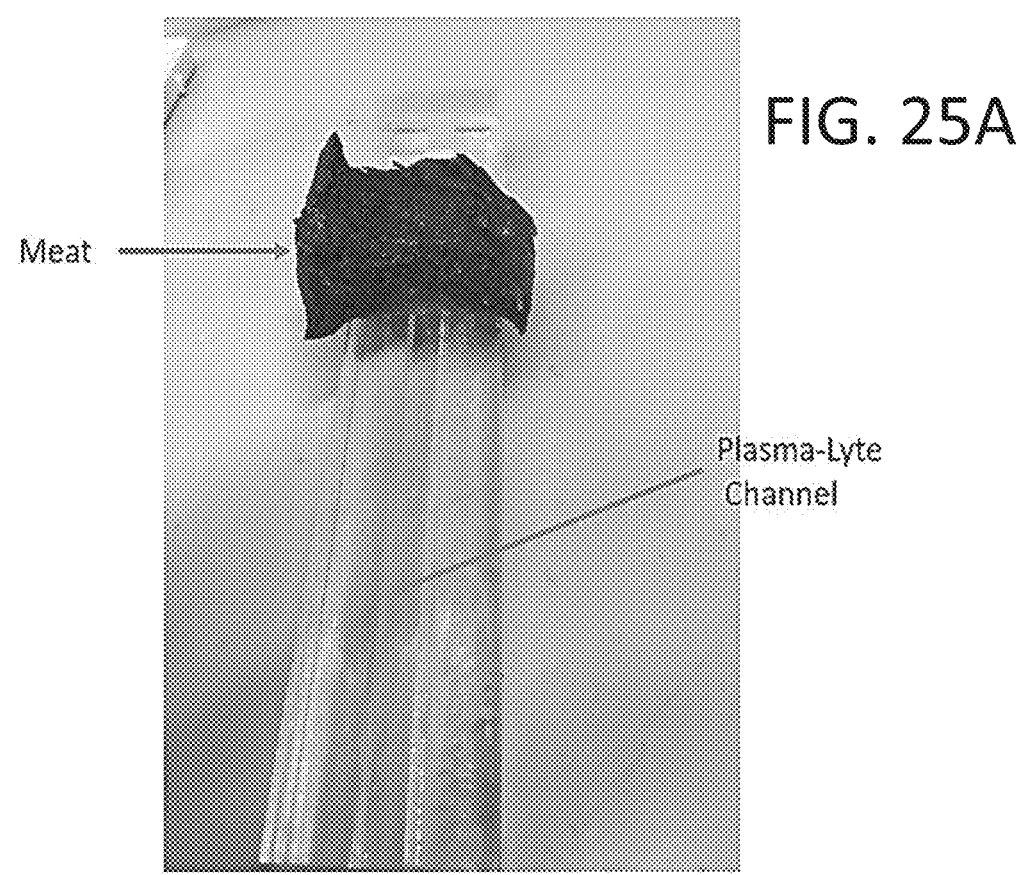
FIGS. 25A and 25B illustrate a test setup using needle-and-wire catheter designs.
Figure 25B:
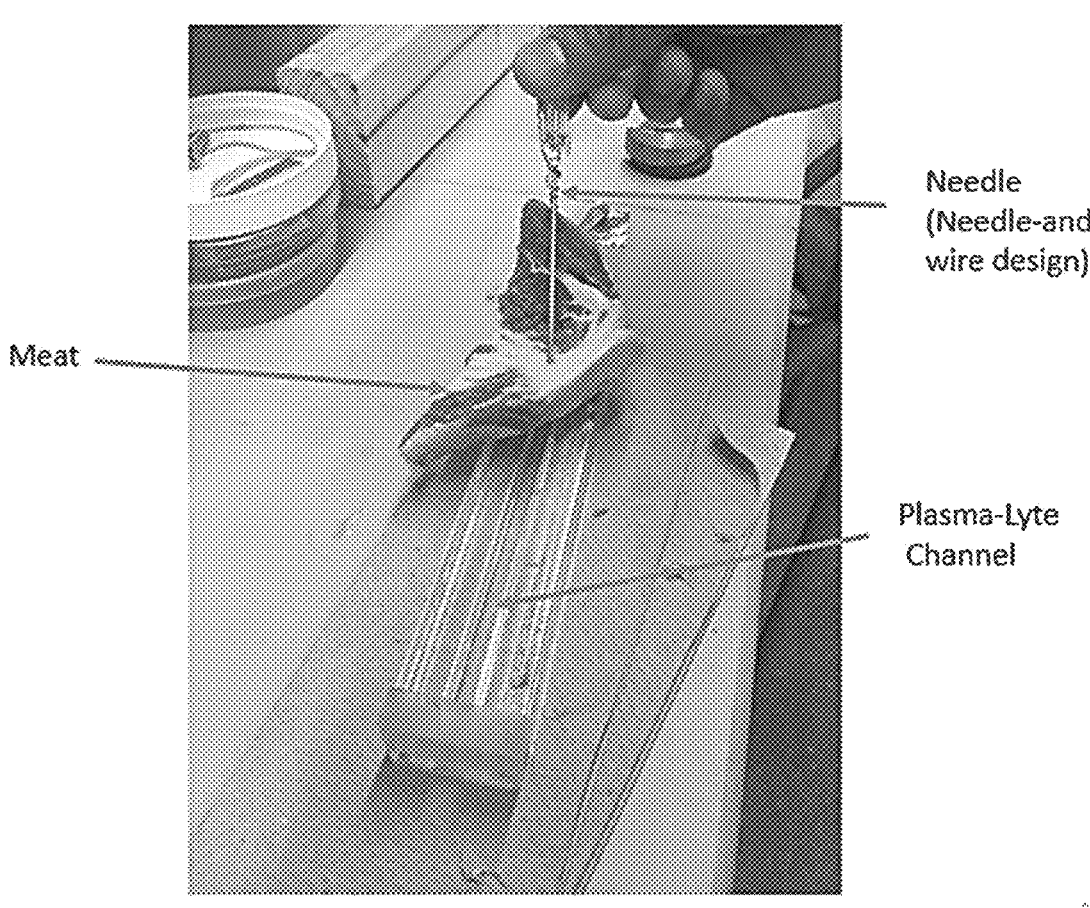

The final test consisted of multi-layer testing where the needle- and-wire catheter assembly shown in FIGS. 25A and 25B traveled through fat prior to entering a Plasma-Lyte A channel in order to simulate real world scenario.

Figure 26:
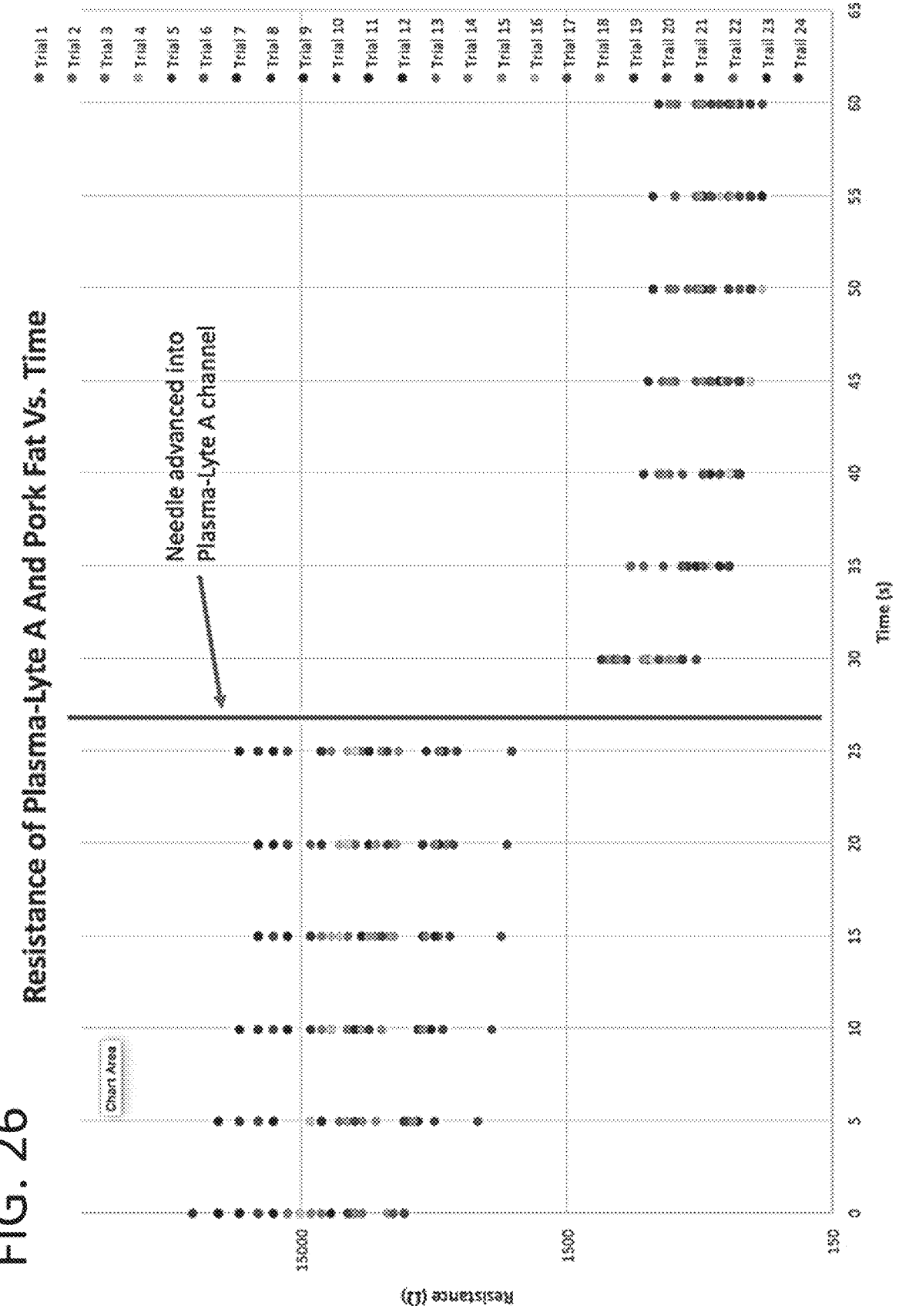
FIG. 26 is a plot of resistance of Plasma-Lyte A and fat vs. time for twenty-four independent trials.
Figure 27:
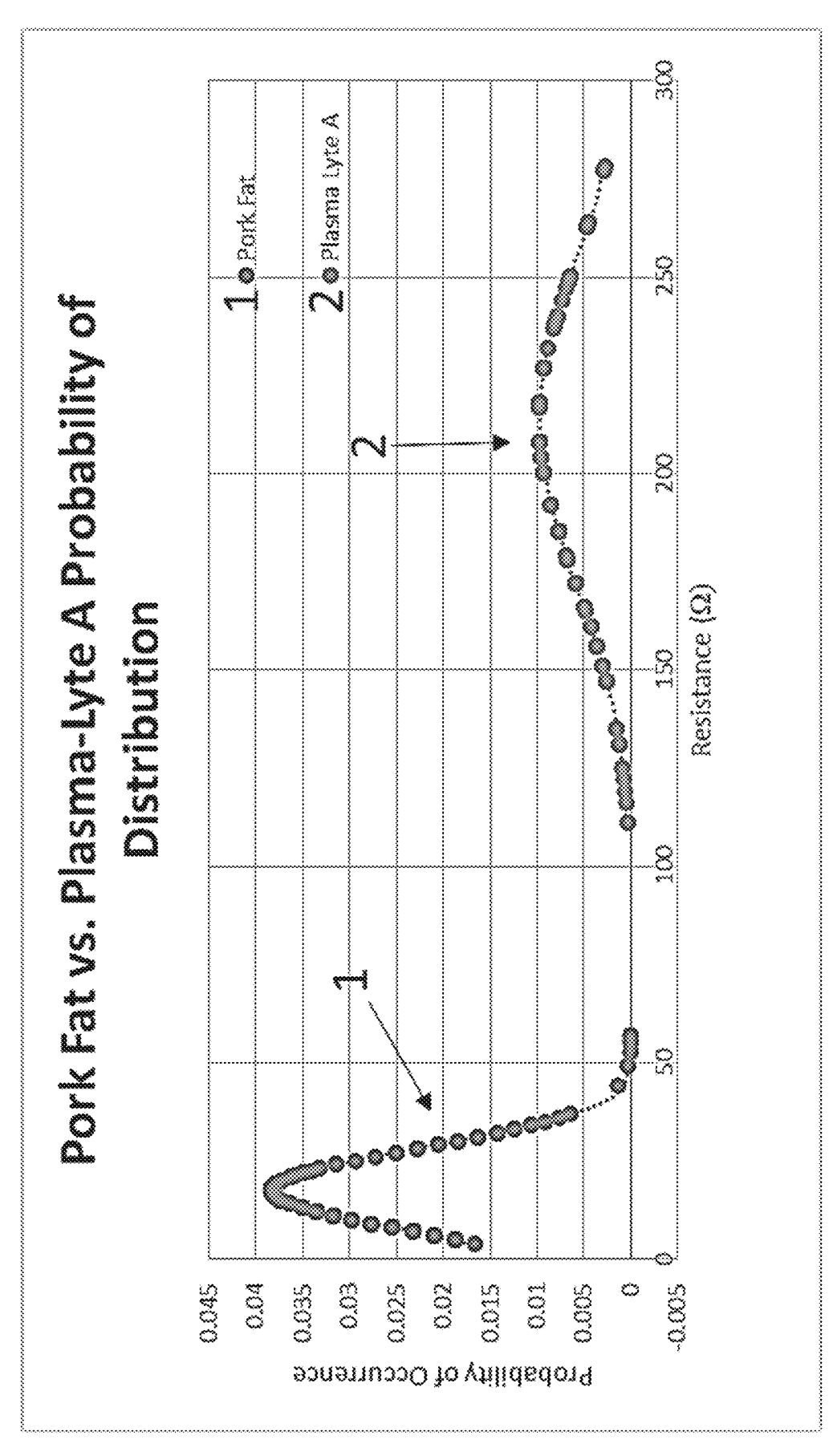
FIG. 27 is a multi-layer probability distribution plot for frequency of pork fat and Plasma-Lyte A for twenty-four independent trials.

FIGS. 25A-25B show the setup for the third test, this served as proof of concept for the overall design. During the test, the needle of the needle- and-wire catheter design was used to first puncture fat for twenty-five seconds, then it was advanced through the layer of fat into the Plasma-Lyte A channel. During the test, the frequency output by oscillator circuit was recorded every five seconds until sixty seconds had elapsed. For the final test, a total of twenty-four trials were conducted in order to assess consistency and repeatability of the method. The results were converted to resistance using Equation 2, and are shown in FIG. 26. From the plots, it can be noted that the measured resistance of pork fat ranged from 2400-38000Ω. Once the needle was advanced into the Plasma-Lyte A channel the resistance value decreased significantly and ranged from 1100-275Ω. Subsequently, the data points were plotted in a probability of distribution plot as shown by FIG. 27. In the plot, the data points were left in terms of frequency's in order to better illustrate the separation between Plasma Lyte A and pork fat. From the plot, it can be noted that the data is normally distributed and we can also make a clear distinction between the two quantities. This provides a large margin permitting reliable differentiation between fatty tissues vs. blood thus allowing rapid detection (e.g. less than 500 ms) of blood vessel entry.

Physicians and nurses place millions of pIV catheters every day in order to administer life-saving medicine in a timely manner. Of those patients about 25% require multiple catheter placement attempts leading to increased pain for the patient, and increased cost associated with the procedure. The disclosed technology provides a solution to reduce the number of first time failures. Several different embodiments are presented herein (e.g., various needle-electrode designs and two detection circuit designs), although other designs are possible to implement the concept. In order to validate the technology, different materials (pork fat, pork shoulder (muscle), and plasma-Lyte A) were initially tested and multi-layer testing was done. The data shows that the technology is successful in detecting a change between fat and plasma-Lyte A.

Embodiments of disclosed technology include can include one or more of the following features:

1) The catheter assembly is modular.
2) The detection unit can differentiate between different materials encountered when placing a catheter.
3) The system can effectively reduce the patient's pain and the cost associated with procedures.
4) The system assists the end user with catheter advancement.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically or chemically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of the following claims.

The invention claimed is:

1. A catheter insertion system, comprising:
   a disposable catheter unit comprising a needle, a guidewire passing through the needle, and a deployable catheter disposed over the needle; and
   a detection unit coupled to the catheter unit, the detection unit comprising circuitry electrically coupled to a first electrode and a second electrode, wherein the needle acts as at least the first electrode, wherein the circuitry comprises a timer circuit and is configured to measure resistance between the first electrode and the second electrode while the catheter unit is inserted into a patient, and wherein the detection unit is configured to determine an anatomical space within which an end portion of the catheter unit is located within the patient based on the measured resistance.

2. The catheter insertion system of claim 1, wherein the second electrode comprises the guidewire.

3. The catheter insertion system of claim 1, wherein a portion of the guidewire within the needle is coated with an electrically insulating material, and an end of the guidewire is left bare.

4. The catheter insertion system of claim 1, wherein the timer circuit comprises a first comparator and a second comparator, and wherein a first output of the first comparator and a second output of the second comparator are connected to a flip flop configured to produce a signal based on a state of the first and second outputs.

5. The catheter insertion system of claim 4, wherein the circuitry comprises a capacitor configured to charge via a voltage provided across resistors, the resistors comprising a first resistor having a predetermine resistance and second resistor having an effective resistance corresponding to material between the first and second electrodes.

6. The catheter insertion system of claim 5, wherein the timer circuit further comprises a transistor connected to receive the signal from the flip flop, and wherein the transistor is configured to open to allow the capacitor to discharge when the signal from the flip flop is a first logical value.

7. The catheter insertion system of claim 5, wherein the signal from the flip flop is provided to an output stage of the timer circuit to produce an oscillating binary output.

8. The catheter insertion system of claim 7, wherein the oscillating binary output is sent to a microcontroller, and wherein a frequency of the oscillating binary output is dependent on relative values of the resistors and the capacitor and is used to determine the measured resistance.

9. The catheter insertion system of claim 5, wherein the first output is based on a comparison of a first input voltage to a first reference voltage, wherein the second output is based on a comparison of a second input voltage to a second reference voltage, and wherein the first and second reference voltages are respective percentages of the voltage provided across the resistors.

10. The catheter insertion system of claim 9, wherein the first reference voltage is a lower percentage of the voltage provided across the resistors than the second reference voltage.

11. A catheter insertion system, comprising:
    a disposable catheter unit comprising a needle, a guidewire passing through the needle, and a deployable catheter disposed over the needle; and
    a detection unit coupled to the catheter unit, the detection unit comprising circuitry electrically coupled to a first electrode and a second electrode located in or on the needle, wherein the circuitry comprises a timer circuit configured to measure resistance between the first electrode and the second electrode while the catheter unit is inserted into a patient, and wherein the detection unit is configured to determine an anatomical space within which an end portion of the catheter unit is located within the patient based on the measured resistance.

12. The catheter insertion system of claim 11, wherein the guidewire comprises two staggered wires inside of the needle acting as the first electrode and the second electrode, respectively.

13. The catheter insertion system of claim 12, wherein each of the two staggered wires lie inside of the needle and are separated from one another by a distance.

14. The catheter insertion system of claim 12, wherein the two staggered wires are housed inside of a single insulated sheath.

15. The catheter insertion system of claim 12, wherein the two staggered wires are inter-wrapped with one another.

16. The catheter insertion system of claim 12, wherein the two staggered wires are insulated to prevent a short circuit between the two staggered wires.

17. The catheter insertion system of claim 16, wherein an inside of the needle is coated with an insulating material.

18. The catheter insertion system of claim 11, wherein the timer circuit comprises a first comparator and a second comparator, and wherein a first output of the first comparator and a second output of the second comparator are connected to a flip flop configured to produce a signal based on a state of the first and second outputs.

19. The catheter insertion system of claim 18, wherein the circuitry comprises a capacitor configured to charge via a voltage provided across resistors, the resistors comprising a first resistor having a predetermined resistance and second resistor having an effective resistance corresponding to material between the first and second electrodes.

20. The catheter insertion system of claim 19, wherein the signal from the flip flop is provided to an output stage of the timer circuit to produce an oscillating binary output, wherein the oscillating binary output is sent to a microcontroller, and wherein a frequency of the oscillating binary output is dependent on relative values of the resistors and the capacitor and is used to determine the measured resistance.

* * * * *